United States Patent
Korporaal

(10) Patent No.: US 11,020,081 B2
(45) Date of Patent: Jun. 1, 2021

(54) METHOD AND SYSTEM FOR DETERMINING A MEASUREMENT START TIME

(71) Applicant: Siemens Aktiengesellschaft, Munich (DE)

(72) Inventor: Johannes Georg Korporaal, Forchheim (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 1083 days.

(21) Appl. No.: 14/892,221

(22) PCT Filed: May 7, 2014

(86) PCT No.: PCT/EP2014/059279
§ 371 (c)(1),
(2) Date: Nov. 19, 2015

(87) PCT Pub. No.: WO2014/195077
PCT Pub. Date: Dec. 11, 2014

(65) Prior Publication Data
US 2016/0089100 A1    Mar. 31, 2016

(30) Foreign Application Priority Data
Jun. 7, 2013 (DE) .......................... 102013210613.0

(51) Int. Cl.
*A61B 6/00* (2006.01)
*A61B 5/055* (2006.01)
(Continued)

(52) U.S. Cl.
CPC .............. *A61B 6/541* (2013.01); *A61B 5/055* (2013.01); *A61B 5/145* (2013.01); *A61B 5/7278* (2013.01);
(Continued)

(58) Field of Classification Search
CPC ......... A61B 5/055; A61B 6/032; A61B 6/481; A61B 6/541; A61B 5/145; A61B 5/7278; A61B 6/504; A61B 6/54; A61B 8/543
See application file for complete search history.

(56) References Cited

U.S. PATENT DOCUMENTS

| 4,611,340 | A | * | 9/1986 | Okazaki | ................. A61B 6/469 |
| | | | | | 348/E5.089 |
| 5,509,412 | A | * | 4/1996 | Bahn | ..................... A61B 5/055 |
| | | | | | 324/306 |

(Continued)

FOREIGN PATENT DOCUMENTS

| CN | 1689515 A | 11/2005 |
| CN | 1820710 A | 8/2006 |

(Continued)

OTHER PUBLICATIONS

International Search Report PCT/ISA/210 for International Application No. PCT/EP2014/059279 dated Sep. 4, 2014.
(Continued)

*Primary Examiner* — Malina D. Blaise
(74) *Attorney, Agent, or Firm* — Harness, Dickey & Pierce, P.L.C.

(57) ABSTRACT

A method is disclosed for determining a measurement start time for an imaging measurement via a medical imaging system depending on a course of concentration values of a contrast medium in a monitored region of an examination object over time. The method includes detecting the concentration values of the current concentration of the contrast medium in the monitored region at different successive detection times; determining a current examination-specific accumulation model curve on the basis of a course of the concentration values over time; and determining the measurement start time on the basis of the examination-specific accumulation model curve. A method for controlling a (Continued)

medical imaging system, a control device and a medical imaging system for implementing the method are further disclosed.

27 Claims, 8 Drawing Sheets

(51) Int. Cl.
*A61B 5/145* (2006.01)
*A61B 5/00* (2006.01)
*A61B 6/03* (2006.01)
*A61B 8/08* (2006.01)
*A61B 8/00* (2006.01)

(52) U.S. Cl.
CPC .............. *A61B 6/032* (2013.01); *A61B 6/481* (2013.01); *A61B 6/504* (2013.01); *A61B 6/54* (2013.01); *A61B 8/481* (2013.01); *A61B 8/543* (2013.01)

(56) References Cited

U.S. PATENT DOCUMENTS

| | | | |
|---|---|---|---|
| 5,687,208 A | 11/1997 | Bae et al. | |
| 6,337,992 B1 | 1/2002 | Gelman | |
| 7,606,614 B2 | 10/2009 | Licato | |
| 9,050,055 B2 | 6/2015 | Korporaal | |
| 2002/0035326 A1* | 3/2002 | Kamiyama | G01S 7/52098 600/437 |
| 2003/0097076 A1* | 5/2003 | Nambu | A61B 6/481 600/504 |
| 2004/0027124 A1* | 2/2004 | Abe | G01R 33/563 324/306 |
| 2005/0245813 A1 | 11/2005 | Kiefer | |
| 2006/0239917 A1* | 10/2006 | Klotz | A61B 6/481 424/9.3 |
| 2006/0239918 A1* | 10/2006 | Klotz | A61B 6/481 424/9.3 |
| 2006/0241402 A1 | 10/2006 | Ichihara et al. | |
| 2007/0055148 A1 | 3/2007 | Klingenbeck-Regn | |
| 2008/0097196 A1* | 4/2008 | Licato | A61B 6/481 600/431 |
| 2008/0183475 A1 | 7/2008 | Hirota | |
| 2008/0253505 A1 | 10/2008 | Imai | |
| 2010/0204572 A1* | 8/2010 | Kalafut | A61B 6/507 600/431 |
| 2011/0130668 A1 | 6/2011 | Ohyu et al. | |
| 2011/0208046 A1 | 8/2011 | Gonzalez Molezzi | |
| 2012/0027180 A1* | 2/2012 | Tsuchiya | A61B 6/4233 378/114 |
| 2012/0242871 A1* | 9/2012 | Iwashita | H04N 5/32 348/241 |
| 2013/0012814 A1* | 1/2013 | Taguchi | A61B 6/481 600/431 |
| 2013/0066198 A1* | 3/2013 | Grant | A61B 6/032 600/428 |
| 2013/0324845 A1 | 12/2013 | Korporaal | |
| 2014/0219539 A1* | 8/2014 | Yoshikawa | A61B 8/06 382/134 |
| 2015/0050218 A1* | 2/2015 | Giavazzi | A61K 49/10 424/9.3 |

FOREIGN PATENT DOCUMENTS

| | | |
|---|---|---|
| CN | 102665563 A | 9/2012 |
| CN | 103445799 A | 12/2013 |
| CN | 102012209410 A1 | 12/2013 |
| DE | 69631607 T2 | 12/2004 |
| DE | 69734785 T2 | 8/2006 |
| DE | 102005006659 A1 | 8/2006 |
| JP | 2008067935 A | 3/2008 |
| JP | 2008259679 A | 10/2008 |
| WO | WO 2010111457 A1 | 9/2010 |

OTHER PUBLICATIONS

Written Opinion of the International Searching Authority PCT/ISA/237 for International Application No. PCT/EP2014/059279 dated Sep. 4, 2014.
Kyongtae T. Bae.: "Intravenous Contrast Medium Administration and Scan Timing at CT: Consideration and Approaches", in: Radiology, vol. 256, No. 1, Jul. 2010, pp. 32-61, DOI:10.1146/radiol.10090908/-/DC1; 2010.
German Office Action dated Jan. 20, 2014.
Chinese Office Action and English translation thereof dated Sep. 25, 2017.

* cited by examiner

METHOD AND SYSTEM FOR DETERMINING A MEASUREMENT START TIME

PRIORITY STATEMENT

This application is the national phase under 35 U.S.C. § 371 of PCT International Application No. PCT/EP2014/059279 which has an International filing date of May 7, 2014, which designated the United States of America and which claims priority to German patent application number DE 102013210613.0 filed Jun. 7, 2013, the entire contents of which are hereby incorporated herein by reference.

FIELD

At least one embodiment of the present invention generally relates to a method for determining a measurement start time for an imaging measurement via a medical imaging system as a function of a behavior of concentration values of a contrast medium in a monitored region of an examination subject over time. At least one embodiment further generally relates to a method for activating a medical imaging system, to a control device and/or to a medical imaging system for implementing the methods according to at least one embodiment of the invention.

BACKGROUND

Contrast media provide enhanced visualization of structures and functions of a living examination subject or body in imaging methods such as diagnostic radiology (e.g. computed tomography), magnetic resonance tomography (MRT) and sonography (ultrasound). Contrast media which absorb X-rays more strongly than normal soft tissue are often used in diagnostic radiology in order to visualize blood vessels in the body (angiography). When an iodine-containing solution is employed as a contrast medium, the blood vessels into which the solution is delivered attenuate the X-rays more than the surrounding tissue and thus increase the image contrast of the blood vessels. An increased concentration value of the contrast medium therefore makes itself noticeable in a directly linear manner with an increase in the attenuation value measured in a measurement operating with X-ray radiation. In that respect the terms "concentration value" and "attenuation value" or "X-ray attenuation value" may also be used synonymously insofar as measurements using X-ray radiation are concerned.

Before a contrast-medium-assisted imaging scan, e.g. a computed tomography acquisition (CT scan), can be carried out, it is necessary for the contrast medium to be present in a sufficient concentration in a target region or target tissue of the body at the time of the CT scan. The target region is, for example, an organ (heart, lung, kidney, etc.) of which image data is to be generated with an interest in obtaining specific findings in mind.

A commonly practiced method of monitoring the progression of a contrast medium concentration (also referred to in the following as "contrast medium behavior"), i.e. an accumulation or enhancement of contrast medium KM and a depletion in the wake of a maximum enhancement (also referred to in the following as "peak concentration phase" KG), is explained with reference to FIG. 1. FIG. 1 shows a diagram containing three time axes (I, II, III) running horizontally and parallel to one another. A topogram TP, a "pre-monitoring" phase PM, a "bolus tracking scan" BTS and a main measurement HS of an examination subject P are plotted on a bottom time axis (III). The topogram TP serves to register a location of a target region ZB and a monitored region UB in an examination subject P. The bolus tracking scan BTS is performed in the monitored region UB, and the target region ZB is subsequently scanned in the main measurement HS. The purpose of the pre-monitoring phase PM, which takes place before the contrast medium is injected, is to define, in the monitored region UB, a region in the body, in most cases the aorta, where the bolus tracking scan is evaluated and if necessary the native attenuation value of the blood is determined.

A behavior of a contrast medium concentration C(t) in the examination subject P is shown in a very roughly simplified representation (as a simple triangular function) on a middle time axis (II). A contrast medium delivery function IF(t) which extends over a contrast medium administration period IZ is shown on a top time axis (I). The three time axes (I, II, III) are correlated with one another with respect to time. In this method the "bolus tracking scan" BTS is performed prior to the commencement of the actual main scan HS of the target region ZB. Concentration values $KD_1$, $KD_2, \ldots, KD_9$ of the contrast medium (specified in the unit Hounsfield Units (HU)) are measured at specific detection times $t_1, t_2, \ldots, t_9$ separated by equal time intervals, e.g. every second, by the bolus tracking scan BTS. The concentrations are detected in a monitored region of the body that lies in close proximity to the target region which is to be measured in the main scan HS. If, for example, image data of a heart is to be generated in the main scan HS, the bolus tracking scan BTS can be performed in a slice of the ascending aorta.

The bolus tracking scan BTS is therefore started immediately after or with a specific monitoring time delay UZ after administration of the contrast medium at a contrast medium administration start time SK. A contrast medium administration period IZ, i.e. a time period in which a volume of contrast medium is introduced at a specific injection rate into the body, can last longer than a time period taken by the bolus tracking scan BTS. As soon as it is recognized at a detection time $t_1, t_2, \ldots, t_9$ (in this case: $t_7$) that a previously defined concentration threshold value KS of the contrast medium in the monitored region, e.g. 150 HU, has been exceeded, the main scan HS of the target region ZB is usually started after a previously defined scan time offset SZ ("scan delay"), e.g. 3 s after the concentration threshold value KS is reached (a so-called "post-trigger delay").

This method offers a high probability that the contrast medium has arrived in the target region in a minimum enhancement of the HU value (in this case 150 HU) specified in the concentration threshold value KS when the main scan HS is performed.

SUMMARY

The inventors have recognized that the method is subject to a number of disadvantages: The previously defined concentration threshold value is generally set solely on the basis of empirical values or average values. In respect of an individual patient it is therefore unclear in which phase of the progression of the contrast medium concentration according to the previously defined post-trigger delay or scan time delay the main scan will be performed. This is because the behavior of the contrast medium concentration is greatly dependent, inter alia, on the physiology of the particular patient.

It may therefore happen that the scan time delay has not been optimally chosen in advance, and as a result a main scan is performed in which the contrast medium enhancement in the target region either has not yet reached its peak or has already exceeded a maximum contrast medium concentration. In both cases the contrast medium is then used inefficiently: a higher contrast medium concentration, i.e. a better quality of image data, could have been achieved, or the same enhancement could have been achieved using a smaller volume of contrast medium.

Because a behavior of the contrast medium concentration is dependent on a complex interaction between many parameters (including injection parameters, scan parameters and patient-specific parameters) and accordingly may vary greatly, it is difficult to determine an optimal scan time delay in advance. For this reason a substantially standardized scan time delay is usually chosen which if necessary can take into account a current contrast medium administration time period or a period of time taken by the main scan. According to the traditional method it can nonetheless not be predicted with certainty whether a main scan has taken place at a peak of the contrast medium enhancement or in a peak concentration phase.

At least one embodiment of the invention improves a use of the contrast medium in a contrast-medium-assisted imaging measurement.

At least one embodiment of the invention is directed to a method, a control device, and/or a medical imaging system.

The method according to at least one embodiment of the invention relates to a determination of a measurement start time for an imaging measurement via a medical imaging system as a function of a behavior of concentration values of a contrast medium in a monitored region of an examination subject with respect to time, the method comprising:

detecting the concentration values of a current concentration of the contrast medium in each case in the monitored region at different successive detection times;

determining a current examination-specific enhancement model curve on the basis of a behavior of the concentration values with respect to time; and determining the measurement start time on the basis of the examination-specific enhancement model curve.

At least one embodiment of the invention further relates to a method for activating a medical imaging system in order to generate image data of an examination subject, the method comprising:

determining a measurement start time for an imaging measurement as a function of a behavior of concentration values of a contrast medium in a monitored region of the examination subject with respect to time according to the method described hereinabove; and performing an imaging measurement of a target region of the examination subject using the determined measurement start time.

In addition, at least one embodiment of the invention relates to a control device for a medical imaging system having an interface for acquiring or outputting a contrast medium administration start time as well as a start time determination unit. The start time determination unit comprises an input interface for acquiring concentration values of a current concentration of a contrast medium in a monitored region of an examination subject in each case at different successive detection times;

an enhancement model curve determination unit for determining a current examination-specific enhancement model curve on the basis of a behavior of the concentration values with respect to time; and a model curve analysis unit for determining the measurement start time on the basis of the examination-specific enhancement model curve.

At least one embodiment of the invention further relates to a medical imaging system for generating image data of a target region located inside an examination subject, the system comprising a control device as described hereinabove.

Many of the components of embodiments of the inventive control device of the medical imaging system, in particular the start time determination unit, the enhancement model curve determination unit and the model curve analysis unit, can also be embodied as software modules. An implementation of at least one embodiment of the inventive method that is realized largely in software has the advantage that already existing medical imaging systems can easily be upgraded by way of a software update in order to operate in the inventive manner. In that respect the object is also achieved by way of a computer program product which can be loaded directly into a memory of a programmable control device of a medical imaging system and has program code segments for carrying out all steps of at least one embodiment of the inventive method when the program is executed on the control device.

Further particularly advantageous embodiments and developments of the invention will become apparent from the dependent claims as well as from the following description, wherein the independent claims of one claims category can also be developed analogously to the dependent claims of a different claims category and features of different example embodiments can also be combined in order to form further example embodiments.

BRIEF DESCRIPTION OF THE DRAWINGS

The invention is explained once more in greater detail below with reference to example embodiments taken in conjunction with the attached figures. Like components in the different figures are labeled with identical reference numerals. In the figures.

DETAILED DESCRIPTION OF EXAMPLE EMBODIMENTS

Figure 1:
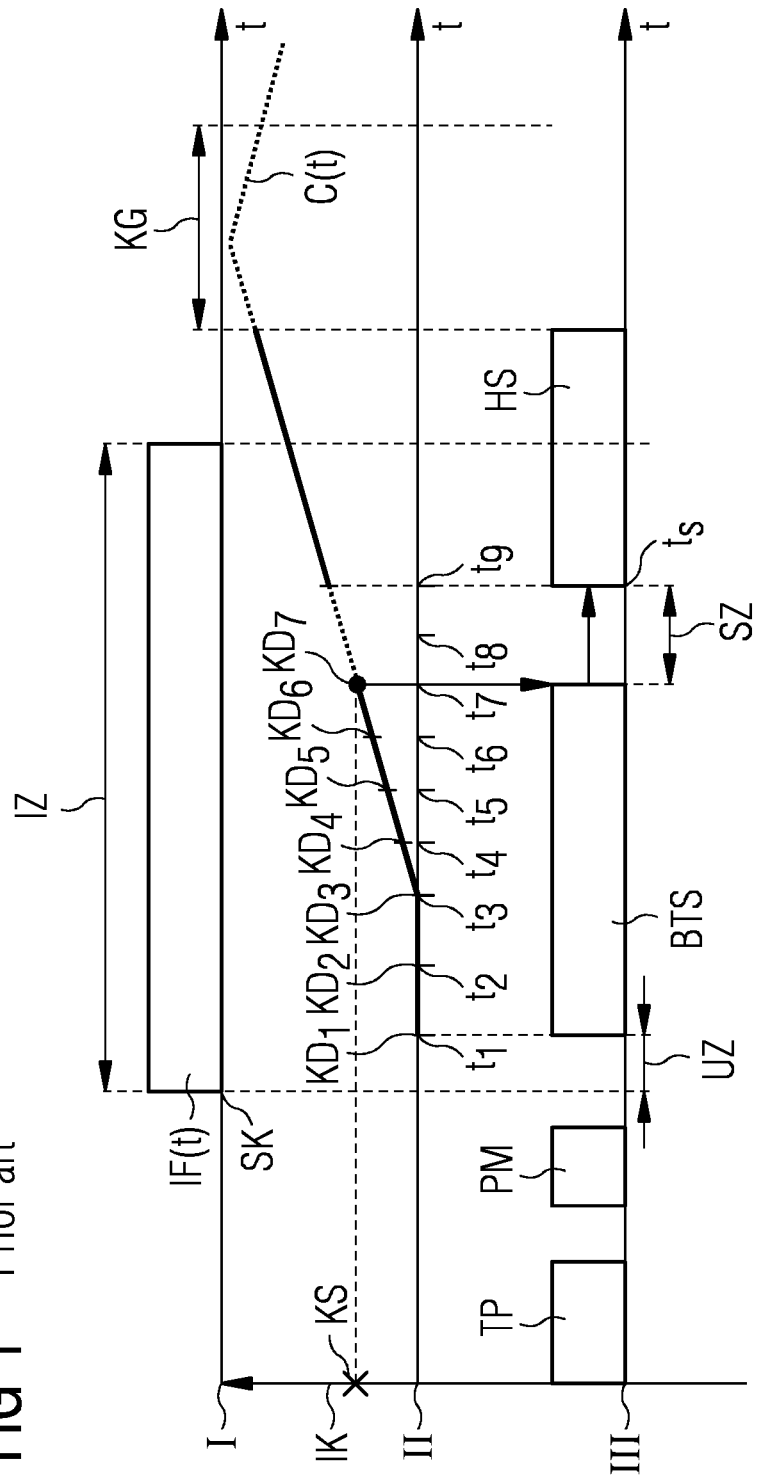
FIG. 1 shows a flowchart of a contrast-medium-assisted scan according to the prior art.

The method according to at least one embodiment of the invention relates to a determination of a measurement start time for an imaging measurement via a medical imaging system as a function of a behavior of concentration values of a contrast medium in a monitored region of an examination subject with respect to time, the method comprising:

detecting the concentration values of a current concentration of the contrast medium in each case in the monitored region at different successive detection times;

determining a current examination-specific enhancement model curve on the basis of a behavior of the concentration values with respect to time; and determining the measurement start time on the basis of the examination-specific enhancement model curve.

What is understood by "imaging measurement" is a production scan or main measurement of a target region of the examination subject which is performed with an interest in obtaining specific findings. A "detection of the concentration values" in the monitored region is understood as a pre-scan or as a pre-measurement of the examination subject. Since concentration values or concentration data of the contrast medium are measured at different successive detection times, preferably in a monitored region that remains identical at all times, e.g. once per second, a main measurement is preceded by at least one pre-measurement, i.e. by five pre-measurements, for example.

The "monitored region" can be different from an imaging target region which is scanned in the main measurement. For example, image data of a patient's heart (as target region) can be generated in the main measurement. In order to determine the measurement start time of the main measurement, concentration values of the contrast medium introduced into the patient can be acquired beforehand in the ascending aorta (as monitored region). Alternatively, the monitored region can also be identical with the target region of the main measurement or be a part of the same. In this case the concentration values can be detected or the pre-measurement and the imaging measurement or the main measurement can be performed by any desired medical imaging system, preferably a computed tomography system, magnetic resonance tomography system and/or ultrasound system.

The expression "behavior of concentration values with respect to time" implies that detected concentration values of a contrast medium may vary, i.e. rise and/or fall, over the course of time. A behavior of concentration values which is represented e.g. by measured values of contrast medium fractions in a tissue which are acquired in fixed or variable time intervals can be represented e.g. as a curve. A measurement start time of the imaging measurement can be determined as a function of a behavior of the concentration values with respect to time in that it is placed on a specific point of the behavioral curve on the basis of predefined criteria. For example, a phase of enhancement of the contrast medium in the monitored region and/or a phase of depletion can be taken into account in this case in such a way that a main measurement is started with a specific time offset prior to a maximum of the contrast medium enhancement so that in any event the maximum is reached during the main measurement. The start time can also be determined with the inclusion of a start time of a contrast medium administration.

By the "examination-specific enhancement model curve" is understood a calculated model-based curve of the contrast medium enhancement and depletion which is "fitted" specifically to currently detected concentration values. By "fitting" in this context is also understood, as will be explained later, a selection of a suitable enhancement model curve from a collection of already calculated (candidate) enhancement model curves. This means that the enhancement model curve has a curve segment which makes a good fit with the currently detected concentration values and consequently takes into account an actual behavior of the contrast medium concentration recorded in the past. It also has a further curve segment which describes a likely future progression of the contrast medium concentration that was calculated on the basis of specific criteria. The entire enhancement model curve, though more particularly the second curve segment, therefore forms a model-like prediction of the concentration behavior of the contrast medium in the examination subject.

The measurement start time can be dependent in addition on the planned duration of a main measurement. The duration can be determined for example by a thickness of a sectional image (slice) that is to be generated, for example in the case of a CT scanner e.g. by a ratio of table feed to beam collimation. Particularly preferably, the measurement start time is chosen such that half of the planned scan duration precedes the peak value and half succeeds the peak value of the contrast medium concentration.

Since, in the method according to at least one embodiment of the invention, it is possible, through the determination of a current enhancement model curve which on the one hand provides a complete model function for the further contrast medium profile and on the other hand is specifically determined for the respective examination on the basis of e.g. only a number of first concentration values from a relatively short time interval after the start of the contrast medium administration, i.e. in a first part of the rise segment of the contrast medium profile, to make a particularly precise determination of the measurement start time of the imaging measurement or main measurement without the need for a measurement of further concentration values over a longer time interval (e.g. up to or shortly before reaching the maximum, or even beyond the maximum of the contrast medium behavior). The main measurement can consequently be performed in a time period which guarantees an optimal utilization of an administered volume of contrast medium. This means that, in comparison with traditional methods, say, it may be possible to reduce the amount of contrast medium.

At least one embodiment of the invention further relates to a method for activating a medical imaging system in order to generate image data of an examination subject, the method comprising:

determining a measurement start time for an imaging measurement as a function of a behavior of concentration values of a contrast medium in a monitored region of the examination subject with respect to time according to the method described hereinabove; and performing an imaging measurement of a target region of the examination subject using the determined measurement start time.

The target region of the examination subject is, as mentioned, a region of which image data is to be generated by way of a production scan, that is to say e.g. an organ of a human being. The use of the measurement start time can entail a further processing in any desired manner, e.g. with inclusion of a planned scan duration of the main measurement or a time offset or other correction factor. Preferably the medical imaging system is also activated in such a way that the data acquisition of the imaging measurement or main measurement commences directly at the measurement start time.

Preferably, the method step of determining a measurement start time is terminated when a defined reliability threshold value of the prediction of a future behavior of a contrast medium concentration is reached and/or a maximum delay value which makes the start of a measurement operation necessary e.g. for technical reasons so that a maximum concentration value of the contrast medium is not exceeded without having been used. For example, the maximum delay value can describe a time buffer that is necessary for switching over a computed tomography system being used from a pre-measurement mode for acquiring the concentration values to a main measurement mode for acquiring image data of the examination subject, including e.g. a time period that is required for relocating a patient couch.

In addition, at least one embodiment of the invention relates to a control device for a medical imaging system having an interface for acquiring or outputting a contrast medium administration start time as well as a start time determination unit. The start time determination unit comprises an input interface for acquiring concentration values of a current concentration of a contrast medium in a monitored region of an examination subject in each case at different successive detection times;

an enhancement model curve determination unit for determining a current examination-specific enhancement model curve on the basis of a behavior of the concentration values with respect to time; and a model curve analysis unit for determining the measurement start time on the basis of the examination-specific enhancement model curve.

Preferably, the control device according to at least one embodiment, the invention also comprises a measurement control unit electronically coupled to the start time determination unit for the purpose of performing an imaging measurement of a target region of the examination subject using the determined start time.

At least one embodiment of the invention further relates to a medical imaging system for generating image data of a target region located inside an examination subject, the system comprising a control device as described hereinabove.

Many of the components of embodiments of the inventive control device of the medical imaging system, in particular the start time determination unit, the enhancement model curve determination unit and the model curve analysis unit, can also be embodied as software modules. An implementation of at least one embodiment of the inventive method that is realized largely in software has the advantage that already existing medical imaging systems can easily be upgraded by way of a software update in order to operate in the inventive manner. In that respect the object is also achieved by way of a computer program product which can be loaded directly into a memory of a programmable control device of a medical imaging system and has program code segments for carrying out all steps of at least one embodiment of the inventive method when the program is executed on the control device.

Further particularly advantageous embodiments and developments of the invention will become apparent from the dependent claims as well as from the following description, wherein the independent claims of one claims category can also be developed analogously to the dependent claims of a different claims category and features of different example embodiments can also be combined in order to form further example embodiments.

Preferably, the examination-specific enhancement model curve is determined on the basis of a population-averaged enhancement model curve and/or a population-averaged contrast medium impulse response function. What is understood by the "population-averaged enhancement model curve" or a "population-averaged contrast medium impulse response function" is a model-based curve which forms an average value of a plurality of empirically acquired, i.e. actually measured, behaviors with respect to time of a contrast medium concentration or contrast medium impulse response function, respectively. In this case the behaviors in relation to a plurality of patients were acquired and e.g. stored in a database. If the underlying patient group is sufficiently large, the population-averaged enhancement model curve or contrast medium impulse response function can possess a high statistical significance with regard to an average behavior of a contrast medium concentration in a human being.

The population-averaged enhancement model curve or contrast medium impulse response function can be individualized by way of a correction factor that is formed e.g. on the basis of examination-specific data pertaining to the examination or measurement that is to be performed, where appropriate even patient-specific data of the current patient/test subject on whom the imaging measurement is to be completed later, and processed further to obtain an examination-specific enhancement model curve. By this method, an examination-specific enhancement model curve can be generated which predicts with a substantial probability an actual behavior of an enhancement or depletion of contrast medium in an examination subject. In this case a population-averaged enhancement model curve can be determined e.g. initially on the basis of the population-averaged contrast medium impulse response function and on that basis then the examination-specific enhancement model curve, or, as will be explained in more detail, an examination-specific enhancement model curve is determined directly on the basis of a population-averaged contrast medium impulse response function.

According to a preferred embodiment variant, injection protocol data is acquired on the basis of which the examination-specific enhancement model curve is determined. The injection protocol data describes actual conditions of an administration or delivery of contrast medium to the examination subject or to the body of a patient. Included in the data is information about a start time, a duration or an end time of a contrast medium administration as well as about a delivery rate of the contrast medium. In particular it is possible to determine an examination-specific enhancement model curve using a combination of a population-averaged contrast medium impulse response function and the injection protocol data.

Thus, on the assumption that a human patient is a linear, time-invariant system, an enhancement model curve C(t) which includes the injection protocol data can be described as a convolution of a contrast medium delivery function IF(t) with a contrast medium impulse response function AIR(t):

$$C(t)=IF(t) \otimes AIR(t) \qquad (1)$$

where the contrast medium delivery function IF(t) represents the injection protocol data. If a patient-individual or examination-specific contrast medium impulse response function AIR(t) were known, an examination-specific enhancement model curve could be calculated immediately. Otherwise a population-averaged contrast medium impulse response function AIRPOP–AVG(t) can be used, such as e.g. in a preferred method according to an embodiment of the invention.

According to a further preferred embodiment variant, the examination-specific enhancement model curve is selected from a plurality of candidate enhancement model curves on the basis of the behavior of the concentration values with respect to time. The candidate enhancement model curves can be calculated prior to the selection step, e.g. using the current injection protocol data and the population-averaged contrast medium impulse response function. They represent possible behaviors of a contrast medium concentration for a number and preferably for a majority of virtual candidates (or virtual patients). Consequently, the candidate enhancement model curves can virtually imitate physiological differences that can characterize different candidates. Preferably, the candidate enhancement model curves take into account a broad, particularly preferably almost the entire, spectrum of human physiologies that may lead to an enhancement or depletion of contrast medium in the body at different rates and/or intensities. The calculation thereof can be based e.g. on criteria such as age, size and weight.

The selection of the candidate enhancement model curves for determining the examination-specific enhancement model curve can be realized e.g. by "fitting" to the concentration values acquired prior to a time of the selection according to known methods. With each further detection of concentration values of a contrast medium behavior, a probability can accordingly increase that a candidate enhancement model curve selected as an examination-specific enhancement model curve will correspond to a future actual contrast medium behavior.

This method offers the advantage that the candidate enhancement model curves can be calculated and stored prior to an examination, in particular even prior to an administration of a contrast medium to a patient. As a function of current concentration values, only the detected concentration values are compared with points of the candidate enhancement model curves corresponding in time and a best-fit candidate enhancement model curve is selected. Compared to a likewise possible completely new calculation of an examination-specific enhancement model curve in real time during a bolus tracking scan or, as the case may be, after each current detection of concentration values, this approach saves on computing power to a considerable degree.

Preferably, the candidate enhancement model curves are parameterized by different widths. In a candidate enhancement model curve, which is a function of the contrast medium intensity values over time, the width of the curve can illustrate how strong a pumping capacity of the heart (also called "cardiac output") of the patient that is to be examined is and how rapidly in consequence a contrast medium introduced into the body of the patient will disperse. The greater a width of the candidate enhancement model curve is, the lower may be the cardiac output of the currently measured patient. A peak value of the contrast medium concentration in the target region of the body is accordingly reached later than in the case of a patient having a comparatively high cardiac output. A depletion of the contrast medium in the target region may likewise be completed more slowly since the heart distributes the contrast medium more slowly throughout the body. Different widths of the individual candidate enhancement model curves therefore represent a spectrum of possible patients and encompass a multiplicity of physiological characteristics and possibly defects of the patients.

Alternatively or in addition, the candidate enhancement model curves are preferably parameterized by way of at least one correction factor. The correction factor can be an arbitrary factor which can be integrated into an equation for calculating the candidate enhancement model curves. This allows additionally present or acquired data to be processed e.g. in advance, enabling a more individual construction of the candidate enhancement model curves or ultimately of the examination-specific enhancement model curve. One or more correction factors can be formed e.g. from parameters which indicate how a patient that is currently to be examined differs from a virtual "population-averaged patient", e.g. by gender, weight or physical capacity.

The correction factor of the candidate enhancement model curves is preferably chosen in each case so that candidate enhancement model curves having different widths possess a substantially identical integral value. An identical integral value or an area of equal size under the curve in a comparison of a plurality of candidate enhancement model curves represents the assumption that a virtual body of a "population-averaged patient", exactly like a body of an individual patient, constitutes a closed system.

On the basis of this assumption, the correction factor brings about a reciprocal change in an amplitude of a candidate enhancement model curve when its width is changed. For example, given a greater width of the curve by the factor bn and consequently a longer temporal dimension, a correction factor of the type leads to a reduction in the height of the curve and consequently in the contrast medium intensity value. With the inclusion of such a correction factor $(1/b_n)$, the candidate enhancement model curves $C_{Kn}(t)$ can be formed e.g. as follows:

$$C_{Kn}(t) \otimes (1/b_n) \cdot a_{AVG} \cdot AIR(t_0+b_n \cdot t) \qquad (2)$$

where $a_{AVG}$ is a population-averaged scaling factor which scales the amplitude of the function and $t_0$ is a parameter by which the curve can be shifted in time. n is simply an index for the nth candidate enhancement model curve.

According to another preferred embodiment variant, a further correction factor is based on a current iodine concentration of the contrast medium and/or on a current tube voltage of a computed tomography system used in the current measurement of the examination subject. Both an iodine concentration of a contrast medium and a tube voltage at which the examination subject is irradiated with X-rays via a radiography system in the course of a measurement substantially influence attenuation values of the X-ray radiation in a tissue of the examination subject that is charged with contrast medium. They accordingly influence a measurement of a contrast medium intensity value. Including one of these values or both values in a calculation of the candidate enhancement model curves or the examination-specific enhancement model curve therefore leads to a more precise approximation of the model curve to an actual behavior of a contrast medium concentration.

Preferably also included in a calculation of the candidate enhancement model curves or the examination-specific enhancement model curve in addition to a current iodine concentration of the contrast medium and/or to a current tube voltage of a radiography system used are, analogously thereto, values of iodine concentrations and/or values of tube voltages on which patient-individual enhancement curves are based, on the basis of which a population-averaged enhancement curve has been formed. For example, an iodine concentration value coAVG used in the determination of the population-averaged contrast medium impulse response function can be placed into a relation with a current iodine concentration value coU used in the pending examination, and/or an iodine vector fKVAVG used in the determination of the population-averaged contrast medium impulse response function can be placed into a relation with a current iodine vector fKVU used in the pending examination. The so-called "iodine vector" is a tube-voltage-value-dependent constant which specifies which tube voltage of the X-ray source leads to which attenuation values at a given iodine concentration. It can lie e.g. at 80 kV for approx. 40 and at 120 kV for approx. 25. The values are preferably determined for the system actually used in practice.

In a development of the equation (2), the candidate enhancement model curves $C_{Kn}(t)$ can be formed with the inclusion of the described correction factors ($co_U/co_{AVG}$; $fKV_U/fKV_{AVG}$) e.g. as follows:

$$C_{Kn}(t) = IF(t) \otimes (1/b_n) \cdot a_{POP\_AVG} \cdot AIR(t_0 + b_n \cdot t) \cdot co_U/co_{AVG} \cdot fKV_U/fKV_{AVG} \qquad (3)$$

Alternatively, instead of using the correction factors b and 1/b in equations (2) or (3), experimentally determined data can also be called upon for the correction.

Furthermore, the method according to at least one embodiment of the invention can preferably be developed in such a way that the examination-specific enhancement model curve is determined by an adjustment of the population-averaged enhancement model curve and/or an adjustment of candidate enhancement model curves to fit the behavior of the concentration values with respect to time. The adjustments of the curves to fit the concentration values detected at specific times can be accomplished in any desired manner, e.g. by scaling, shifting, etc.

The selection of one or more examination-specific enhancement model curves from the candidate enhancement model curves by synchronization with the concentration values detected at specific times or by fitting thereto can be carried out in this case e.g. by arbitrary known fit methods which operate with different optimization algorithms.

According to a preferred embodiment variant, the fitting of the population-averaged enhancement model curve and/or a fitting of candidate enhancement model curves to the behavior of the concentration values with respect to time comprises at least one of the following mathematical operations:

shifting of the population-averaged enhancement model curve and/or of the candidate enhancement model curves relative to the concentration values in respect of a reference concentration value (i.e. a shifting in terms of height, i.e. in the direction of the contrast medium intensity scale)

and/or shifting of the population-averaged enhancement model curve and/or of the candidate enhancement model curves relative to the concentration values in respect of a reference time (i.e. a shifting in the time direction).

The first-cited mathematical operation is based on the fact that the native X-ray attenuation values of the blood of a patient can be different even without the existence of a contrast medium in the blood. This means that the measured values vary and can fluctuate irregularly around an average value, the X-ray attenuation value of native patient blood (i.e. a virtual 0-line). The average value can be determined e.g. by dividing a sum of acquired measured values of the patient blood (prior to the action of a contrast medium) by the number of measurement operations. The virtual average value is referred to in this context as a reference concentration value (or in this case usually in concrete form as a concentration of 0). Preferably, the reference concentration value is set equal to zero by the shift so that only a significant increase in the concentration values, which is then caused by the successive enhancement of the blood with contrast medium, goes beyond the newly defined zero line. The population-averaged enhancement model curve and/or the candidate enhancement model curves are therefore shifted upward along the contrast medium intensity value axis, in the case of radiological imaging e.g. to a level of an X-ray attenuation value (HU value) corresponding to the X-ray attenuation value of native patient blood.

The second-cited operation can be performed in addition or alternatively to the first-cited operation. The population-averaged enhancement model curve and/or the candidate enhancement model curves can preferably be synchronized with one another in a preceding step by being shifted along the time axis such that they all run through a last current measurement point of the contrast medium concentration. The measurement point is understood in this case as a reference time.

Following the synchronization, the population-averaged enhancement model curve and/or each of the candidate enhancement model curves can then be shifted along the time axis and a model curve which best fits the detected concentration values can be determined therefrom.

Particularly preferably, the fitting is effected merely by way of the described simple shift in the time direction and/or by way of a shift in terms of height, i.e. in the direction of the contrast medium intensity scale. Such a simple shift considerably reduces the computing overhead for the fitting. It has also been demonstrated that a more extensive adjustment, in particular in the case of a method in which a suitable examination-specific enhancement model curve can be selected from a sufficiently large number of (population-averaged and varied in respect of the width) candidate enhancement model curves, is unnecessary.

In particular, the selection of one or more examination-specific enhancement model curves from the candidate enhancement model curves can be carried out by synchronization with the concentration values detected at specific times or by the adjustment of the examination-specific enhancement model curves to fit the concentration values using arbitrary known fit-quality determination methods. The latter include, for example, the least squares method, the mean squared error method, the sum of squared errors method or the sum of absolute errors method. Model curves having a particularly low residual can subsequently be used as examination-specific enhancement model curves.

It is possible on the one hand always to analyze all of the candidate enhancement model curves calculated in advance for each new measurement point and to make a selection of a particular examination-specific enhancement model curve only in the final step. On the other hand it is also possible, as the measurement and analysis operations progress, to limit the selection to that enhancement model curve which fits the current behavior of the concentration values particularly well according to a predefined criterion. By reducing the analysis operations it is possible to save on computing power.

It is furthermore possible, in a development of the invention, to use gender-specific and/or weight-specific and/or size-specific and/or defect-specific and/or age-specific population-averaged enhancement model curves and/or contrast medium impulse response functions. In this case the defect-specific population-averaged contrast medium impulse response function or enhancement model curve can represent characteristics of one or more different diseases and be further differentiated. A dedicated population-averaged contrast medium impulse response function and/or enhancement model curve can be formed in each case for each of the cited physiological patient groups. Accordingly, the candidate enhancement model curves can therefore be calculated on group-specific contrast medium impulse response functions. If a plurality of the described group-specific population-averaged contrast medium impulse response functions or enhancement model curves are available, then it is possible to make a preselection from the population-averaged contrast medium impulse response functions or enhancement model curves on the basis of a patient's diagnostic findings prior to a main measurement of a patient.

It is assumed in the following example embodiments that the imaging system is a computed tomography system (CT system) which can be used for a CT angiography procedure, for example. It is, however, expressly pointed out that the invention is not limited to an application on computed tomography systems, but can also be used with other medical imaging systems, for example magnetic resonance systems or ultrasound systems or other types of computed tomography systems.

FIG. 1 has already been described in the introduction.

Figure 2:
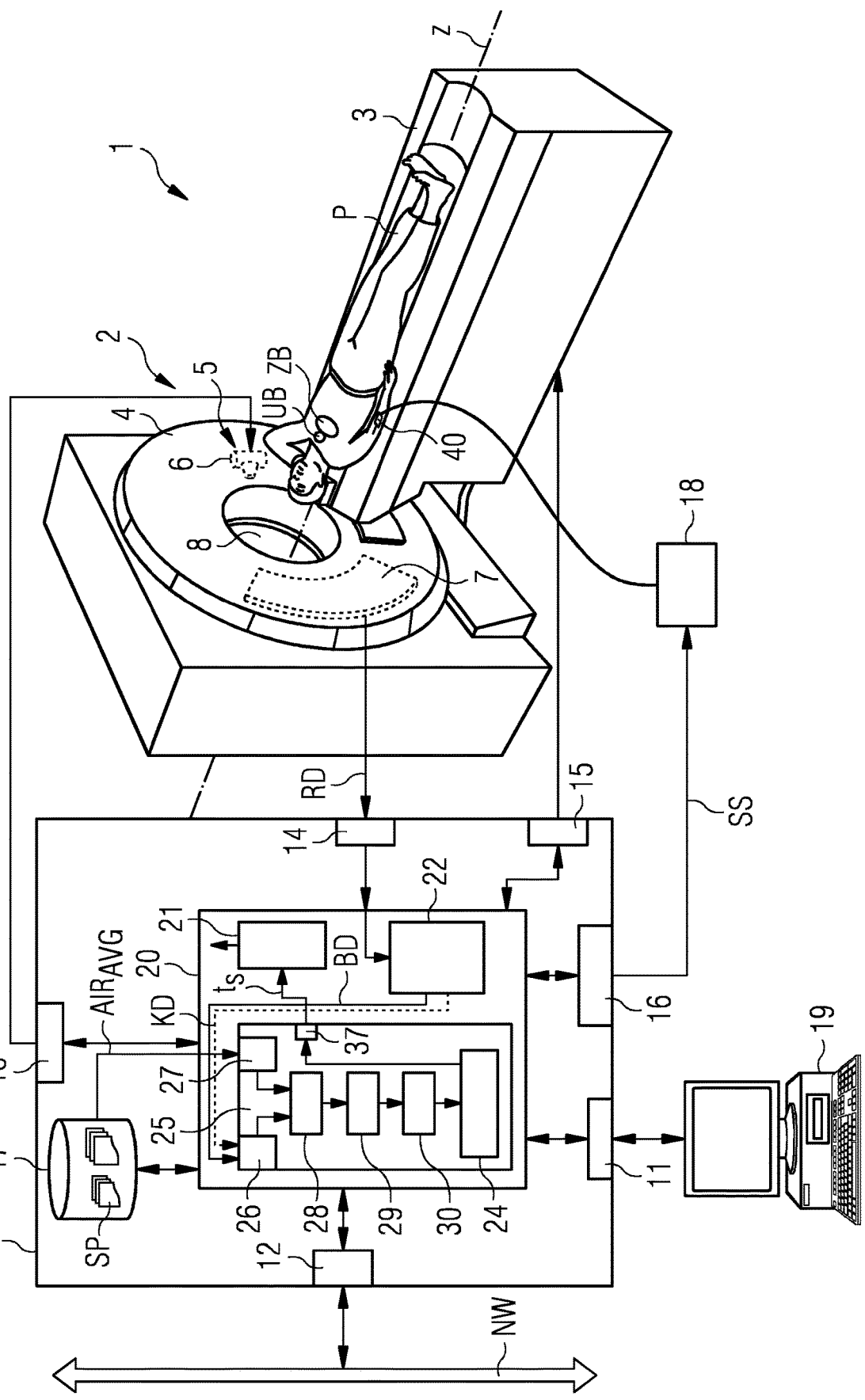
FIG. 2 shows a schematic view of an imaging system having an embodiment variant of an inventive device for performing the inventive method.

FIG. 2 shows an example embodiment of a CT system 1 comprising an inventive device 25 for determining a measurement start time. In this configuration the CT system 1 has a central control and processing device 10 and a scanner unit 2.

The scanner unit 2 comprises a patient table 3 and a gantry housing 4 in which a raw data acquisition device 5 having a gantry-mounted rotatable X-ray source 6 as well as an oppositely arranged gantry-mounted rotatable detector array 7 is installed around an examination zone 8. An examination subject P, in this case a test subject or patient P, is supported on the patient table 3 and can be introduced into the examination zone 8 along a system axis (or axis of rotation) z.

It is also expressly pointed out that the computed tomography system 1 illustrated in FIG. 1 is merely an example embodiment and the invention can of course also be used in systems in which the gantry moves along the patient P or test subject P and the latter lies at a fixed position on the patient table 3.

Other types of detectors can also be used, for example detectors extending along the entire circumference, which remain stationary, while only the X-ray source 6 rotates. Variants having a plurality of X-ray sources or other configurations are also possible.

In the illustrated example embodiment the patient P or test subject is a human being. In principle, however, the method can also be applied to animals, i.e. the term test subject P or patient P is accordingly to be interpreted in a wide sense.

A contrast medium can be administered to the test subject P or patient P by way of an injection needle 40, wherein the flow rate of the contrast medium can be controlled by a contrast medium administration unit 18 as a function of time in accordance with a precisely defined input function that is prescribed for example in an injection protocol.

The gantry 4 together with its components is controlled via the central control and processing device 10, which comprises a processor 20 and a plurality of interfaces 11, 12, 13, 14, 15, 16 as well as a memory 17. A plurality of cooperating processors can of course also be used instead of a single processor 20.

A terminal 19 for operator control of the computed tomography system 1 is connected via a first output/input interface 11. A further output/input interface 12 serves for connecting to a network NW, for example an RIS network (RIS=Radiological Information System) and/or a PACS network (PACS=Picture Archiving and Communication System). Image data and/or raw data can be transmitted over the network NW to mass storage devices, output units, diagnostic review stations, workstations or the like.

Signals can be transmitted via a control interface 13 by way of a control line to the gantry 4 and the X-ray source 6 in order to activate these in an appropriate manner. For the sake of simplicity, a common control interface 13 is shown merely schematically for all control functions relating to the gantry 4.

In order to generate the respective scan images in the desired manner, an activation unit 21, which is implemented in the form of software, is also contained on the processor 20. In order to activate the scanner 2 for a specific measurement, the activation unit 21 imports specific scan protocols SP from the memory 17, for example. A control and processing unit 10 for a computed tomography system typically has a memory 17 containing a plurality of such scan protocols SP for a wide range of different examination situations, an operator being able to select and if necessary modify a suitable scan protocol SP in each case via the terminal 19. After the measurement is started, the entire CT system 1 then operates in accordance with control parameters in the selected scan protocol SP. However, the operator can control and activate the entire CT system 1 at any time via the terminal 19.

Raw data RD, that is to say projection measurement data, is acquired via a raw data acquisition interface 14 by way of a data line from the detector array 7 at specific, for example selected, times. The measured raw data RD is transmitted to an image reconstruction unit 22 which generates image datasets therefrom and writes the same into, for example, DICOM files or other image files, which are then available for a variety of other functions. The functions include e.g. storing in the internal memory 17 or in an external storage medium by way of the network NW, displaying on the screen of the terminal 19, but also automatic evaluation, for example a segmenting and/or determining of contrast medium enhancement values in a previously defined body region of interest. This region may for example have been defined manually by an operator by use of a graphical user interface after having been displayed on the terminal 19. Automatic selection of the body region is also possible, however.

As will be explained in more detail later (see FIG. 3), the region of interest or, as the case may be, a target region ZB of the patient P can be scanned in a main measurement HS. A pre-measurement in preparation for the main measurement HS, e.g. in order to track a contrast medium enhancement behavior, can be carried out in a monitored region UB of the patient P which—as shown here—can be located very close to the target region ZB. If image data BD of the heart of the patient P as target region ZB is to be acquired e.g. in the production scan or main measurement HS, the premeasurement can be performed at the ascending aorta as monitored region UB.

The table feed of the patient table 3 can be controlled via a further control interface 15 in a matching manner to the control of the gantry 4, the X-ray source 6 and the detector array 7 in order thereby, for example, to acquire raw data RD from the desired region of the examination subject P in accordance with the particular control protocol in a sequential method or in a helical method (spiral method) and to reconstruct the image data BD therefrom. In this case both individual slices and volume data can be acquired.

Via a further output/input interface 16 it is possible, by way of the control and processing unit 10, to activate the external contrast medium administration unit 18 in synchronism with the further units of the CT system 1. Toward that end a start signal SS can be transmitted by the control and processing unit 10 to the contrast medium administration unit 18. The interface 16 enables e.g. in particular also the information concerning the injection protocol (such as the contrast medium concentration, the flow rate, the volume, etc.) to be transmitted from the control and processing unit 10 to the external contrast medium administration unit 18 or vice versa. Alternatively, the contrast medium administration unit 18 can also be part of the control and processing unit 10.

In the example embodiment shown, a measurement start time determination unit 25 for automatically determining a measurement start time of a main measurement of the examination subject P is implemented in the processor 20 of the control and processing unit 10. The measurement start time determination unit 25 has an input interface 26 for importing image data BD and if necessary concentration values KD which can optionally be determined by the image reconstruction unit 22 from the image data BD. In addition, the measurement start time determination unit 25 also has an input interface 27 for importing a number of population-averaged enhancement model curves and/or contrast medium impulse response functions, which can be stored for example in the memory 17. It also receives the above-cited information about the injection protocol.

The measurement start time determination unit 25 additionally comprises a candidate curve calculation unit 28 for generating a number of candidate enhancement model curves on the basis of a population-averaged contrast medium impulse response function, a fitting unit 29 for fitting the candidate enhancement model curves to the examination-specific concentration values, an enhancement model curve determination unit 30 for determining a current examination-specific enhancement model curve on the basis of the fitting, and a model curve analysis unit 24 for determining a measurement start time ts on the basis of the examination-specific enhancement model curve. The measurement start time determination unit 25 is connected via an output interface 37 to the activation unit 21, to which the measurement start time ts is transferred and which thereupon activates the scanner 2 accordingly.

The precise mode of operation of the measurement start time determination unit 25 will be explained in more detail later with reference to FIGS. 4 to 12.

The image reconstruction unit 22, the measurement start time determination unit 25 and the model curve analysis unit are implemented here in the form of software on the processor 20. In principle, however, all of these units can also be realized at least in part as hardware components.

It is clear that a CT system 1 used for embodiments of the invention can also have in addition a plurality of further standard components, though for reasons of simplicity these are not depicted in further detail in FIG. 2 and also do not require further explanation because they are well-known to the person skilled in the art.

Figure 3:
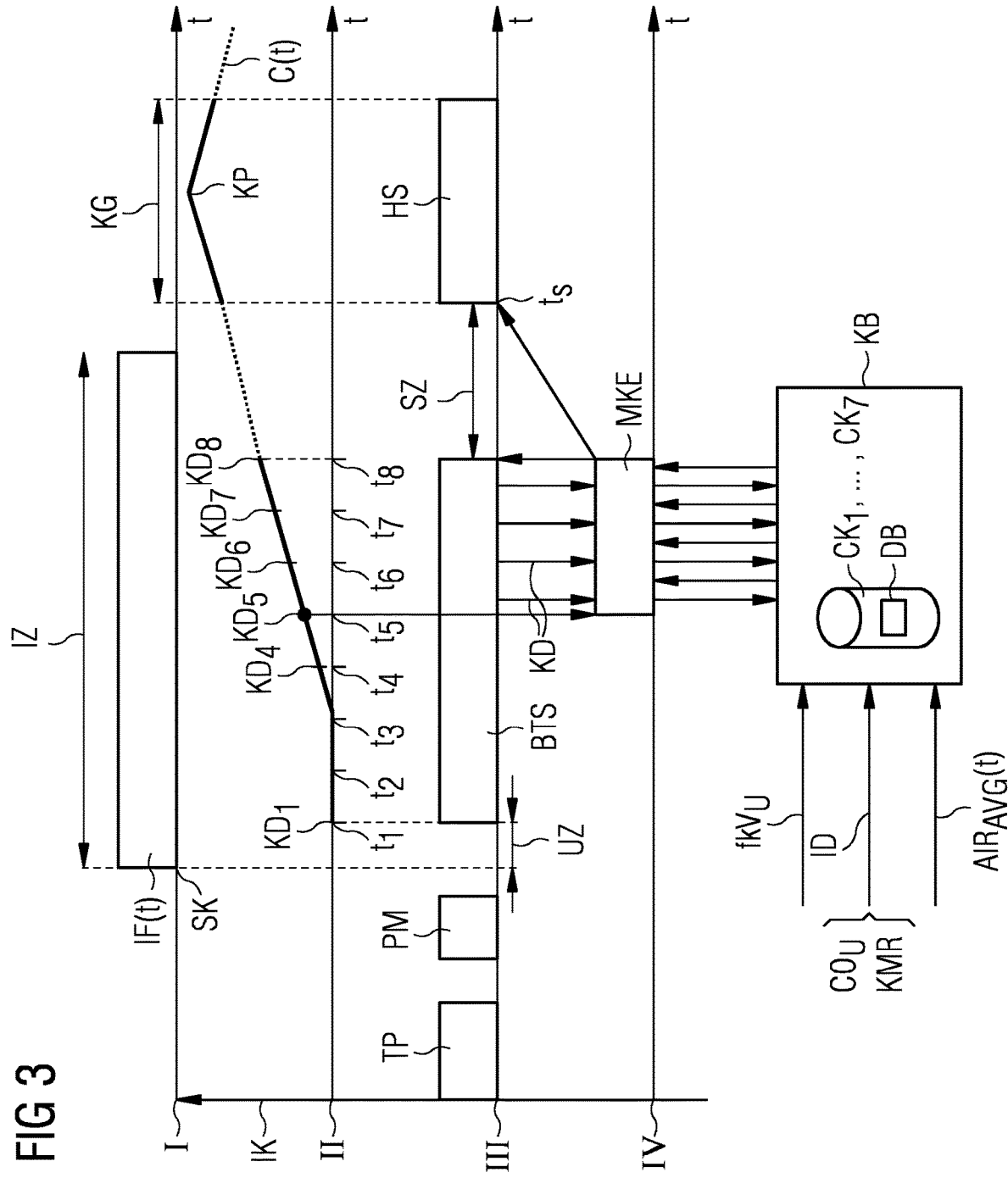
FIG. 3 shows a flowchart of a contrast-medium-assisted scan according to an embodiment variant of the inventive method.

FIG. 3 corresponds in its layout to FIG. 1, with the difference that a fourth time axis (IV) places a calculation period in which one or more examination-specific enhancement model curves $C_M$ are determined within the scope of a model curve determination operation MKE on the basis of the previously measured concentration values $KD_1$, $KD_2, \ldots, KD_5, \ldots, KD_8$ into a temporal relationship with a contrast medium delivery function IF(t), a contrast medium behavior function C(t), a bolus tracking scan BTS and a main measurement HS.

As in FIG. 1, a bolus tracking scan BTS is started immediately after or with a specific monitoring time delay UZ after the administration of the contrast medium KM at a contrast medium administration start time SK. Concentration values $KD_1$, $KD_2$, $KD_3, \ldots, KD_8$ (whose numbering coincides with the number of the corresponding detection times) of the contrast medium KM are now measured in the monitored region UB of the body P at detection times $t_1$, $t_2$, $t_3, \ldots, t_8$. A concentration value $KD_5$, which is the first that significantly exceeds previously acquired measured values $KD_1, \ldots, KD_4$ of the blood, triggers a computing operation which calculates a first current contrast medium behavior function C(t). This calculation takes the place of a performance of the main scan HS of the target region ZB in accordance with a previously defined scan time delay SZ, as is part of the described conventional method.

The computing operation operates with population-averaged enhancement model curves (on the basis of a population-averaged contrast medium impulse response function AIRAVG) which describes a contrast medium enhancement as an average value for a population. A population, in the present context, may be defined as a total population or a gender-specific and/or weight-specific and/or size-specific and/or defect-specific and/or age-specific population. This means that an average value of a specific group of patients is formed for a patient P, the group preferably sharing as far as possible identical physiological characteristics with the patient P in respect of at least one parameter. For example, the group comprises persons of the same sex, having a similar body weight, having a similar body size, or similar in age. The measured values on which the population-averaged enhancement model curve is based can be stored e.g. in a database DB.

Using the population-averaged contrast medium impulse response function, a number of candidate enhancement model curves $C_{K1}$, $C_{K2}, \ldots, C_{K7}$ (see also FIG. 4) which represent possible scenarios of a behavior of a contrast medium concentration with respect to time are calculated in a candidate curve calculation operation KB with the inclusion of a tube voltage constant fkV (derived from the tube voltage of the CT scanner used when determining the population-averaged measured data) and corresponding injection protocol data ID (e.g. containing information on a total amount of contrast medium KM used, an injection rate, and an iodine content of the contrast medium KM). Once they have been calculated, the curves $C_{K1}$, $C_{K2}, \ldots, C_{K7}$ can likewise be stored in the database DB. The selection of a population-averaged contrast medium impulse response function and the calculation of candidate enhancement model curves $C_{K1}, C_{K2}, \ldots, C_{K7}$ can in each case be completed already prior to a contrast medium administration start time SK.

An algorithm which takes into account injection protocol data ID, i.e. at least one contrast medium administration period IZ, a contrast medium injection rate KMR and the current iodine concentration $co_U$ thereof, as well as a currently used tube voltage $fkV_U$, calculates which of the candidate enhancement model curves $C_{K1}, C_{K2}, \ldots, C_{K7}$ is most similar to an actual contrast medium enhancement curve, which in this case is described only by the first significant concentration value $KD_5$ detected at time $t_5$.

The computing operation is iteratively repeated for each further concentration value $KD_6$, $KD_7$, $KD_8$ of the contrast medium KM. After each further detection time $t_6$, $t_7$, $t_8$ corresponding to the concentration values $KD_6$, $KD_7$, $KD_8$, an examination-specific enhancement model curve $C_M$, which is calculated from the family of candidate enhancement model curves $C_{K1}, C_{K2}, \ldots, C_{Kn}$, corresponds with greater reliability to an actual contrast medium enhancement curve. In the case of the present example embodiment, the acquisition of concentration values and the following calculation are aborted at the latest after the acquisition of the eighth concentration value $KD_8$, because a time has been reached which is necessary as a buffer for the activation or configuration of the scanner for a main scan HS. This premature termination of the bolus tracking scan BTS is symbolized by the upward-pointing arrow at the end of the model curve determination operation MKE between the axes IV and III in FIG. 3.

On the basis of the most recently calculated contrast medium behavior function C(t), which is then used as the examination-specific enhancement model curve $C_M$ (see FIG. 7), a measurement start time $t_s$ is now calculated at the start of the main scan HS. The measurement start time $t_s$ takes into account a previously determined duration of the main scan HS and is placed e.g. such that the main scan HS is performed in a peak concentration phase KG which, starting from a calculated peak KP of the contrast medium concentration in the target region ZB, extends in equal parts into the time before the peak KP and the time after the peak KP.

With this method, therefore, an optimum time window for performing the main scan HS of the patient P is determined on the basis of the concentration values KD of the bolus tracking scan BTS in real time in the form of the peak concentration phase KG of the examination-specific enhancement model curve, taking into account all relevant scan parameters, injection parameters ID and patient characteristics. A previous specification of a concentration threshold value KS and a scan time delay SZ are no longer absolutely necessary therefor.

Figure 4:
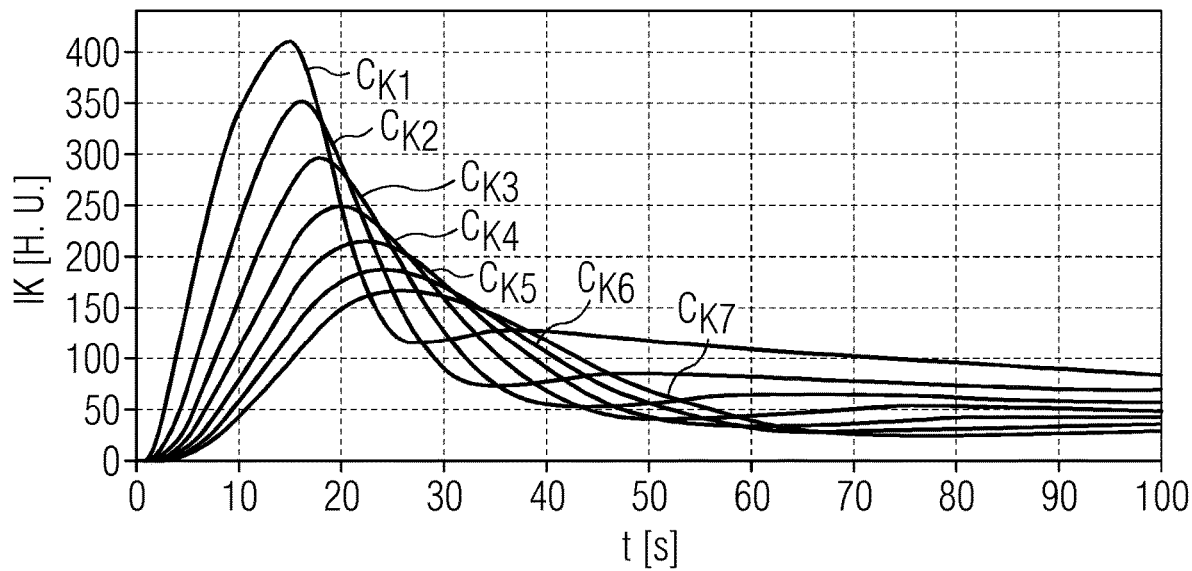
FIG. 4 shows a diagram containing a plurality of candidate enhancement model curves having different width values.

FIG. 4 shows seven candidate enhancement model curves $C_{K1}, \ldots, C_{K7}$, which have been calculated on the basis of a population-averaged contrast medium impulse response function prior to a main measurement HS and stored and which represent possible behaviors of a concentration of contrast medium KM in the body of a patient P. Each of the candidate enhancement model curves $C_{K1}, \ldots, C_{K7}$ is a function of the contrast medium intensity IK (in Hounsfield units HU) over time t (in s). The calculation is carried out for each of the functions $C_{ki}(t)$ (where i=1 to 7) by way of the above-cited equation (3).

In this case different width values bn (where n=1 to 7) are inserted in the equation (3), which here range between 1.0 and 4.0 with increments of 0.5, resulting in the following candidate enhancement model curves CK1, ..., $CK_7$:

$C_{K4}$ for $b_1$=1.0
$C_{K2}$ for $b_2$=1.5
$C_{K3}$ for $b_3$=2.0
$C_{K4}$ for $b_4$=2.5
$C_{K5}$ for $b_5$=3.0
$C_{K6}$ for $b_6$=3.5
$C_{K7}$ for $b_7$=4.0

In this case the different width values $b_1, \ldots, b_7$ represent or imitate in model-like fashion physiological differences of individual patients P whose bodies exhibit different rates of an enhancement/depletion of contrast medium KM. The correction factor $(1/b_n)$ in equation (3) takes into account, as already mentioned above, the fact that a human being forms a closed system and therefore, if there is a change in the width of the contrast medium impulse response function $AIR_{AVG}(t)$, the amplitude changes reciprocally. As a result, as can be seen in FIG. 4, an integral value of the candidate enhancement model curves $CK_1, \ldots, CK_7$ or the areas under the candidate enhancement model curves $CK_1, \ldots, CK_7$ remain identical in each case.

It can be proven experimentally that if the assumption of reciprocity in a measurement of an individual patient P is not fulfilled, an impact of the discrepancy between the model calculation according to the invention and the actual characteristics of an individual patient P on a measurement start time $t_s$ of the main measurement HS is very small. In an examination-specific enhancement model curve $C_M$ there is a change in the amplitude or in absolute contrast medium intensity values IK in this case. Owing to a very similar behavior with respect to time, however, a contrast medium concentration maximum IP determining the peak concentration phase KG lies at a similar point. In that respect the above assumption of reciprocity possesses a general validity.

Alternatively, instead of using the correction factor b and its reciprocal value, 1/b, in equations (2) or (3), it would also be possible to use experimental data which describes the relationship between the width and amplitude of the contrast medium impulse response function by way of a look-up table (LUT).

The calculated or "simulated" candidate enhancement model curves $C_{K1}, \ldots, C_{K7}$ should ideally have a high temporal resolution of e.g. between 0.01 s and 0.001 s in comparison with the temporal resolution of the bolus tracking scan BTS (which in most cases lies at approx. 1 to 2 s in CT measurements).

The equation (3) cited in the introduction takes into account in addition the iodine concentration $co_U$ of the contrast medium KM used in the current measurement in relation to the iodine concentration coAVG which formed the basis for the measurements from which a population-averaged contrast medium impulse response function $AIR_{AVG}(t)$ was calculated.

The values shown in FIG. 4 are furthermore based on injection protocol data ID or on a contrast medium delivery function IF(t) in which, by way of example, a contrast medium volume of 70 ml is introduced into the body P at an injection rate of 5 ml/s, and the contrast medium KM has a concentration of 300 mg iodine/ml. In addition the equation (3) takes into account the iodine vector $fKV_U$ which, as explained above, is dependent on the tube voltage at which a radiological imaging system is operated in the current measurement (or, to be more precise, the bolus tracking scan BTS of the current measurement). This iodine vector $fKV_U$ forms a quotient with the iodine vector $fKV_{AVG}$, which in turn is dependent on the tube voltage which formed the basis for the measurements from which the population-averaged contrast medium impulse response function $AIR_{AVG}(t)$ was formed.

Other parameters which can determine the extent to which an individual patient P is different from the population-averaged values used, such as e.g. heart rate, cardiac output or weight, could also be taken into account in principle in addition in equation (3) by way of dedicated correction factors.

The candidate enhancement model curves $C_{K1}, \ldots, C_{K7}$ show that a comparatively high width value b is reflected in a wider contrast medium impulse response function $AIR(t)$ and a contrast medium concentration maximum IP is in this case reached only after a comparatively longer time. It can be inferred from the curve profile that a patient of the type has a low cardiac output. The physiological characteristics of a patient therefore reveal themselves in this method from a finally selected examination-specific enhancement model curve $C_M$, without the latter having been augmented from the outset with patient-specific parameters.

Figure 5:
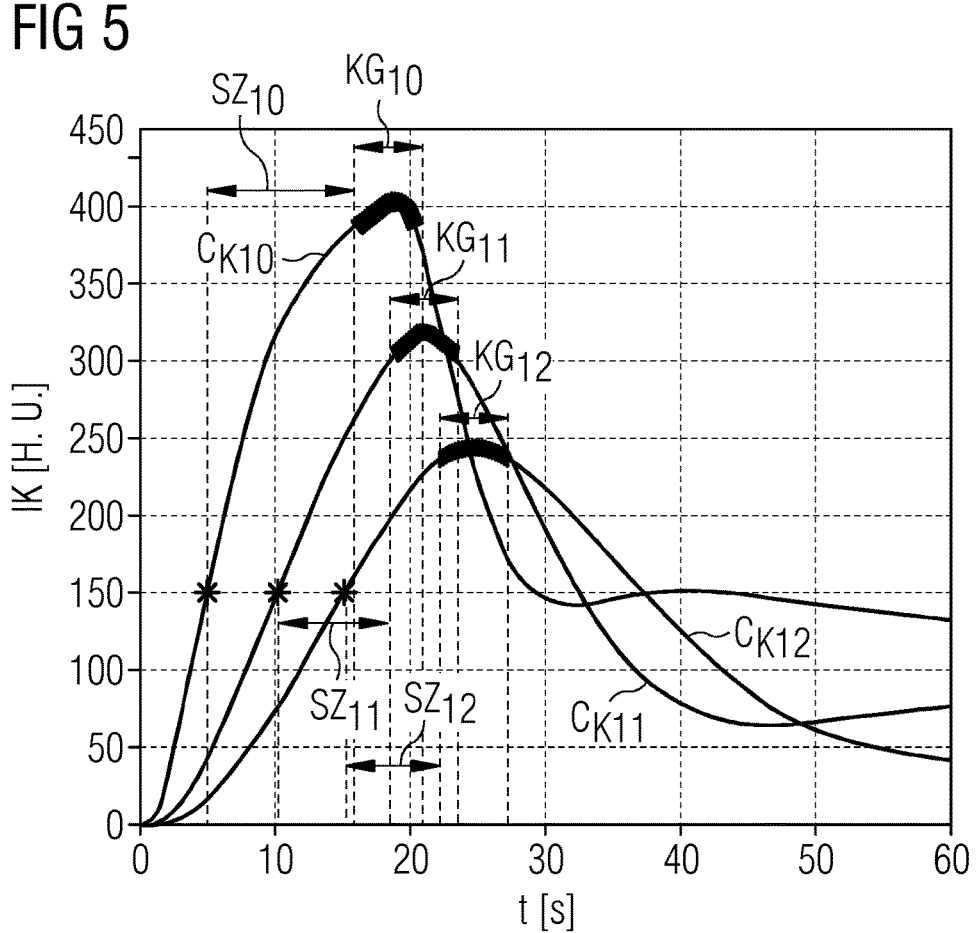
FIG. 5 shows a diagram as in FIG. 4 illustrating further candidate enhancement model curves.

FIG. 5 shows three candidate enhancement model curves $C_{K10}, C_{K11}, C_{K12}$, where width values $b_{10}, b_{11}, b_{12}$ (see FIG. 6 in this regard) of their respective underlying contrast medium impulse response functions $AIR(t)$ are specified with 1.0 ($C_{K10}$), 2.0 ($C_{K11}$) and 3.0 ($C_{K12}$). In this case the injection protocol data ID for calculating these curves indicates by way of example a total volume of contrast medium KM of 90 ml which is introduced into the body of the patient P at an injection rate of 5 ml per second. An iodine concentration $co_U$ of the contrast medium KM used amounts to 300 mg iodine/ml. A tube voltage of an X-ray tube used in the main measurement HS, which tube voltage serves to calculate the tube voltage constant $fkV_U$, amounts to 100 kV.

Taking into account the planned duration of the main scan HS (the duration is yielded e.g. from the scan length and the "pitch", i.e. the ratio of table feed to beam collimation of a CT scanner), a peak concentration phase $KG_{10}, \ldots, KG_{12}$ can be determined for each candidate enhancement model curve $C_{K10}, \ldots, C_{K12}$, i.e. a time period therefore having the duration of the main scan which includes e.g. a maximum contrast medium enhancement IP. The peak concentration phase KG is in this case defined as a time period having the highest enhancement of contrast medium. It can, however, also be defined as a time period before a maximum of the contrast medium enhancement is reached. The second option offers a higher certainty that a thus determined measurement start time $t_s$ of a main measurement HS lies closer to the time as determined according to the traditional method starting from a concentration threshold value KS (see FIG. 1). However, it is also less efficient, since a maximum contrast medium enhancement is not used to the full. In the example described here, the peak concentration phase $KG_{10}, \ldots, KG_{12}$ lasts a predefined 4 s in each case, though it can also be defined shorter or longer, depending on the scan duration of the main scan HS.

According to the prior art method described in FIG. 1, the bolus tracking scans BTS would in each case be terminated at a concentration threshold value KS of 150 HU. A main measurement HS would start automatically after a scan time delay SZ having a fixed value, e.g. of 3 s, had elapsed. However, FIG. 5 shows that a different scan time delay $SZ_{10}$, $SZ_{11}, SZ_{12}$ would be optimal for each of the three candidate enhancement model curves $C_{K10}, \ldots, C_{K12}$. For the candidate enhancement model curve $C_{K10}$ it would be about 11 s, for the candidate enhancement model curve $C_{K11}$ about 9 s, and for the candidate enhancement model curve $C_{K12}$, only about 7 s. This shows that with a scan time delay SZ of e.g. 3 s (as in FIG. 1) a main measurement HS would be completed significantly before a contrast medium concentration maximum IP, and as a result a suboptimal contrast medium enhancement would be reached in the image data BD.

Figure 6:
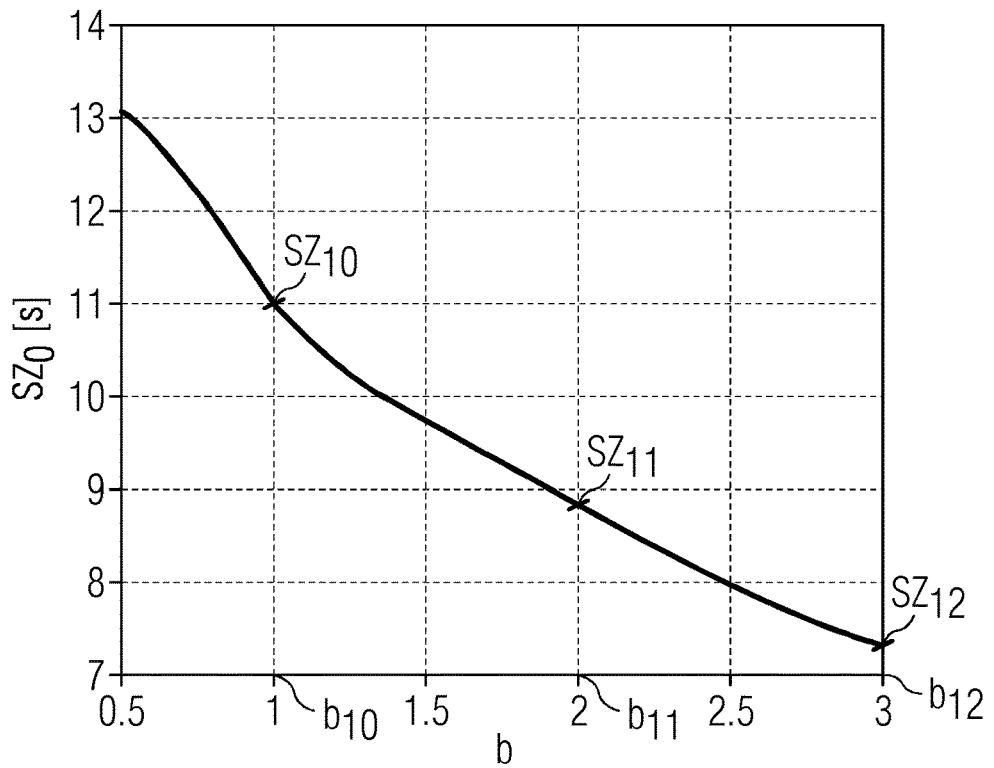
FIG. 6 shows a diagram containing a function of an optimal scan time delay over a width of a contrast medium behavior function.

FIG. 6 illustrates the relationship established in FIG. 5 between a width of the contrast medium impulse response function $AIR(t)$ and an optimal scan time delay $SZ_o$ which indicates a time period between an end of a bolus tracking scan BTS and a measurement start time ts. The greater a width value (b=0.5 to 3.0) of a candidate enhancement model curve $C_K$ or an examination-specific enhancement model curve $C_M$ is, the smaller is a value of an optimal scan time delay $SZ_{10}, SZ_{11}, SZ_{12}$ (these three plotted values correspond in this case in reality to the width values $b_{10}=1$, $b_{11}=2, b_{12}=3$), which in this instance lies between 7 s and 13 s.

Figure 7:
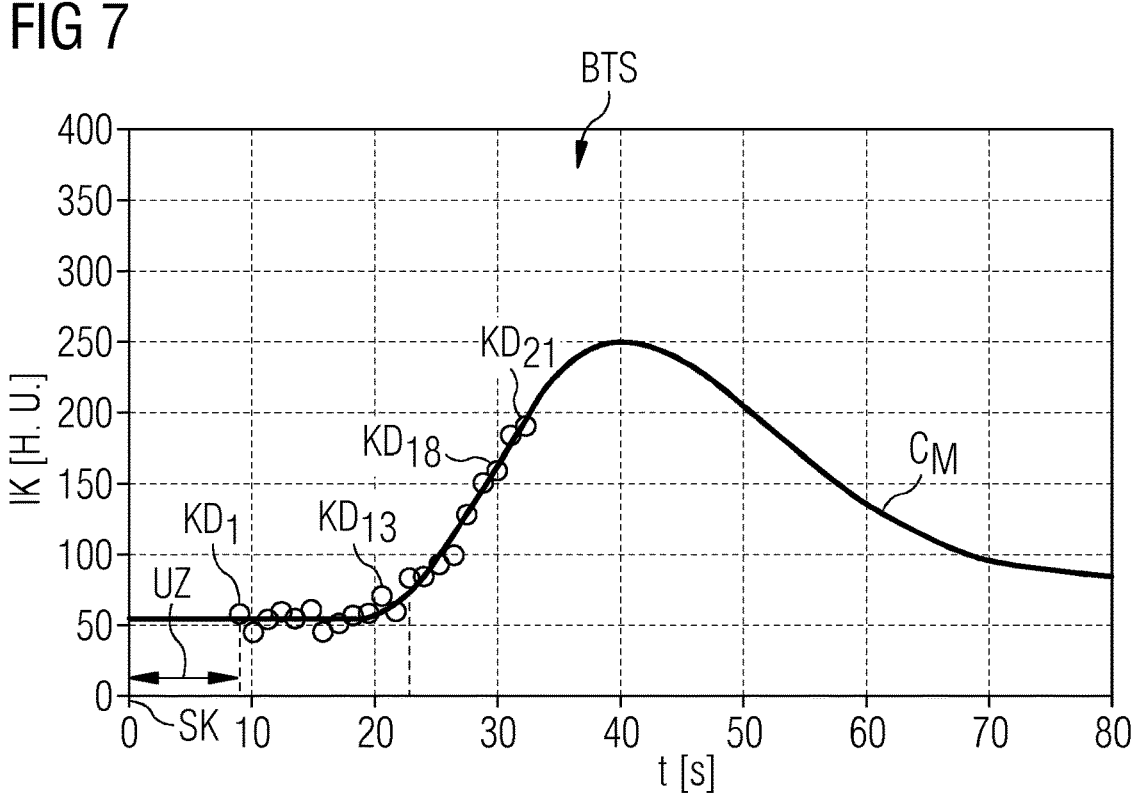
FIG. 7 shows a diagram as in FIG. 4 illustrating concentration values of the bolus tracking scan as well as an examination-specific enhancement model curve determined therefor.

FIG. 7 shows the concentration values $KD_1, KD_2, \ldots, KD_{21}$ detected in the course of the bolus tracking scan BTS in measurement intervals, such as e.g. of is in each case, at measurement times $t_1, t_2, \ldots, t_{21}$. The bolus tracking scan BTS is started with a monitoring time delay UZ, in this case e.g. of about 8 s, after the contrast medium administration start time SK. With the acquisition of the concentration value $KD_{13}$, a previously defined threshold value, in this case e.g. of 30 HU, over a starting level in the form of the previously detected concentration values $KD_1, KD_2, \ldots, KD_{12}$ is reached. The starting level of the concentration values $KD_1, KD_2, \ldots, KD_{12}$ in this case represents a native X-ray attenuation or HU value of the patient blood (which in the present instance lies around approx. 50 HU). A computing operation is started as a result of the threshold value being exceeded. The algorithm used therein (see FIG. 4) determines a current examination-specific enhancement model curve in real time after each measurement $KD_{13}, \ldots, KD_{21}$. Following a final acquisition of concentration values $KD_{21}$, the examination-specific enhancement model curve $C_M$ (see also FIG. 4) is produced on the basis of the detected concentration values $KD_1, \ldots, KD_{21}$. This determination of the examination-specific enhancement model curve $C_M$ is accomplished according to the preferred variant of the method by selection of a candidate enhancement model curve $C_K$ (see below) which is particularly well fitted to the profile of the concentration values KD acquired up to a current detection time (in this case $t_{21}$). The exact procedure for selecting the best-fitting candidate enhancement model curve $C_K$ is explained in more precise detail below with reference to FIGS. 8 to 11.

Figure 8:
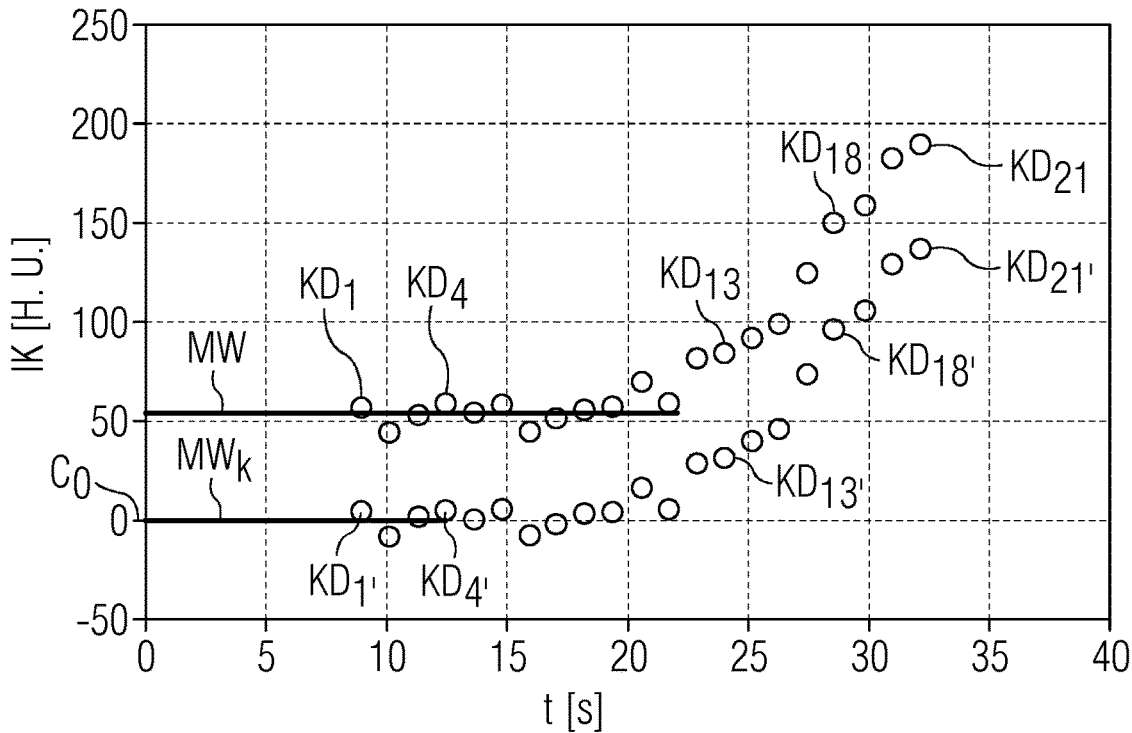
FIG. 8 shows a diagram as in FIG. 4 depicting a zero-line correction of detected concentration values.

Firstly, the concentration values KD or candidate enhancement model curves $C_K$ must be adjusted in such a way that the native X-ray attenuation value or HU value of patient blood in the calculation of an examination-specific enhancement model curve $C_M$ is (implicitly) taken into account. For this purpose a "baseline" or a reference concentration value $C_0$, which is defined by an X-ray attenuation value for pure water at 0 HU, is shifted to an X-ray attenuation value (always to be determined individually) of a blood volume of the patient P to be measured ("baseline offset", i.e. isoelectric line shift). This is illustrated in FIG. 8. If e.g. a blood volume of a patient P has a native value of 50 HU without an introduction of contrast medium KM, and after an introduction of contrast medium KM a concentration value KD of 80 HU is observed in image data BD of the blood, a 30 HU increase in contrast medium results from the difference.

A baseline or zero line having the average value MW (in this case e.g. around approx. 50 HU) is first determined in a pre-monitoring phase for a phase without the action of contrast medium KM. All concentration values KD detected in this phase are then corrected downward to the corrected average value MWk (having 0 HU). All concentration values $KD_1$ to $KD_{21}$ detected in the course of a bolus tracking scan BTS or monitoring scan of an examination subject P with the action of the contrast medium KM are also subsequently corrected downward virtually by 50 HU to concentration values $KD_{1'}$ to $KD_{21'}$.

This is accomplished by way of a shifting of the zero line at an axis of the contrast medium intensity values IK by the same value upward, with the result that the blood of the patient is set equal to 0 HU. The shift can be determined in the pre-monitoring phase and/or from a number of concentration value acquisitions in the monitored region UB, e.g. an average value of the first four acquisitions, for which it can be assumed with absolute certainty that the contrast medium KM has not yet arrived in the monitored region UB.

Alternatively, the simulated candidate enhancement model curves $C_K$ can be increased by the currently determined HU value of the patient blood. This method ultimately leads to the same result. All of the following mathematical operations relate to the increase in the contrast medium concentration or to the concentration value KD' corrected in respect of the baseline offset, and not to the absolute X-ray attenuation or HU values.

Figure 9:
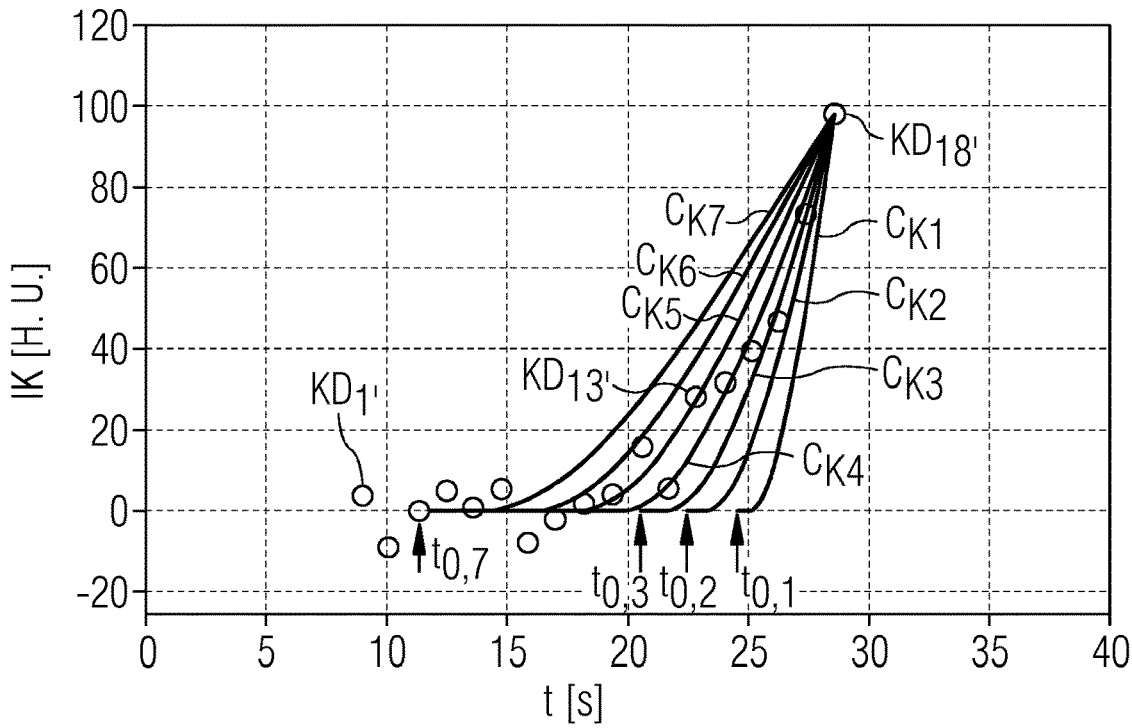
FIG. 9 shows a diagram as in FIG. 4 depicting a synchronization of a plurality of candidate enhancement model curves to one concentration value.

FIG. 9 therefore shows in this regard, as part of an adjustment of candidate enhancement model curves $C_K$ to fit the behavior of detected concentration values KD with respect to time, a graphical representation of a synchronization method. The candidate enhancement model curves $C_{K1}, \ldots, C_{K7}$, which differ from one another by virtue of the width values $b_1, \ldots, b_7$, are in each case shifted along the time axis t in such a way that they all run through a measurement point of the contrast medium concentration $KD_{18'}$ that was detected at a measurement time $t_{18}$. For this purpose the time at which the curve comes closest to the concentration value $KD_{18'}$ is determined separately for each candidate enhancement model curve $C_{K1}, \ldots, C_{K7}$. This step results in reference times $t_0$, different with respect to time or shifted relative to one another, at which the candidate enhancement model curves $C_{K1}, \ldots, C_{K7}$ rise from a virtual zero line. In concrete terms these are in this case $t_{0.1}$ (for $C_{K1}$), $t_{0.2}$ (for $C_{K2}$), $t_{0.3}$ (for $C_{K3}$), $\ldots$, $t_{0.7}$ (for $C_{K7}$).

Figure 10:
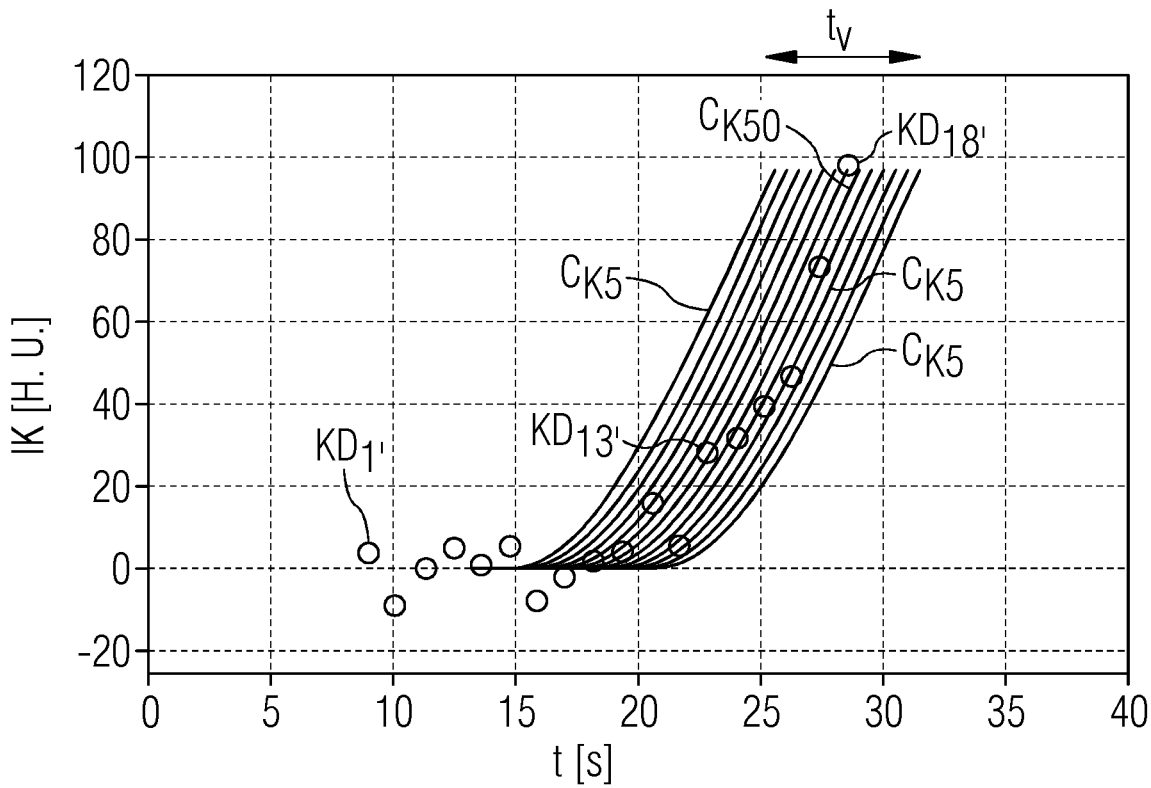
FIG. 10 shows a diagram as in FIG. 4 depicting a shifting of a candidate enhancement model curve along the time axis.

FIG. 10 illustrates the requisite step for determining the best-fitting curves, which is completed directly after the synchronization method according to FIG. 9. The candidate enhancement model curve $C_{K5}$, as an example of each of the candidate enhancement model curves $C_{K1}, \ldots, C_{K7}$ shown in FIG. 9, is shifted by a specific time segment along the time axis, e.g. 3 s, in increments of e.g. 0.1 s past the most recently detected (and corrected in respect of the zero line offset) concentration value $KD_{18'}$. A search is made by way of the least squares method to find a best possible match and consequently an optimal shift with respect to time $t_v$ for the candidate enhancement model curve $C_{K5}$ ($b_5=3.0$).

Following the analysis of the entire time segment, the candidate enhancement model curve $C_{K5o}$ is determined as the curve making the best match. It was achieved by way of a time shift value $t_v$ that has a smallest possible residual in relation to a match with the detected concentration values KD. The actual parameters of the best-fitting candidate enhancement model curve $C_{K5o}$ are then stored: the cited residual ("goodness of fit"), a width value b, the reference time $t_0$, and a time shift value $t_v$. This adjustment step is carried out afresh for each of the candidate enhancement model curves $C_{K1}, \ldots, C_{K7}$ after measurement of each new concentration value KD.

Following the analysis of all previously calculated candidate enhancement model curves $C_{K1}, \ldots, C_{K7}$, a candidate enhancement model curve $C_K$ having the smallest residual is determined. The associated examination-specific enhancement model curve $C_M(t+t_0+t_v)$ is used to predict the contrast medium enhancement following detection of the most recent concentration value KD.

The mean squared error method can, as mentioned, be applied as a fit-quality determination method in order to determine an optimal adjustment of an examination-specific enhancement model curve $C_M$ to fit a behavior of the concentration values KD with respect to time. Alternatively, other similarity methods can also be used, such as e.g. the sum of squared errors or the sum of absolute errors.

Alternatively to an analysis of all of the pre-calculated candidate enhancement model curves $C_K$ after each new acquisition of concentration values KD, with an increasing number of acquisitions, a next iteration in each case can be restricted to those candidate enhancement model curves $C_K$ which in a preceding adjustment in accordance with a specific threshold value best fitted the concentration values KD acquired thus far. This offers the advantage of a stepwise reduction in necessary computing capacities.

This method is repeated for as long as the bolus tracking scan BTS continues to run. The reliability of the prediction increases after each succeeding acquisition of concentration values KD in the course of the bolus tracking scan BTS, since the current examination-specific enhancement model curve $C_M$ at a given time will always include one concentration value KD more than the respective previously completed calculation.

Figure 11:
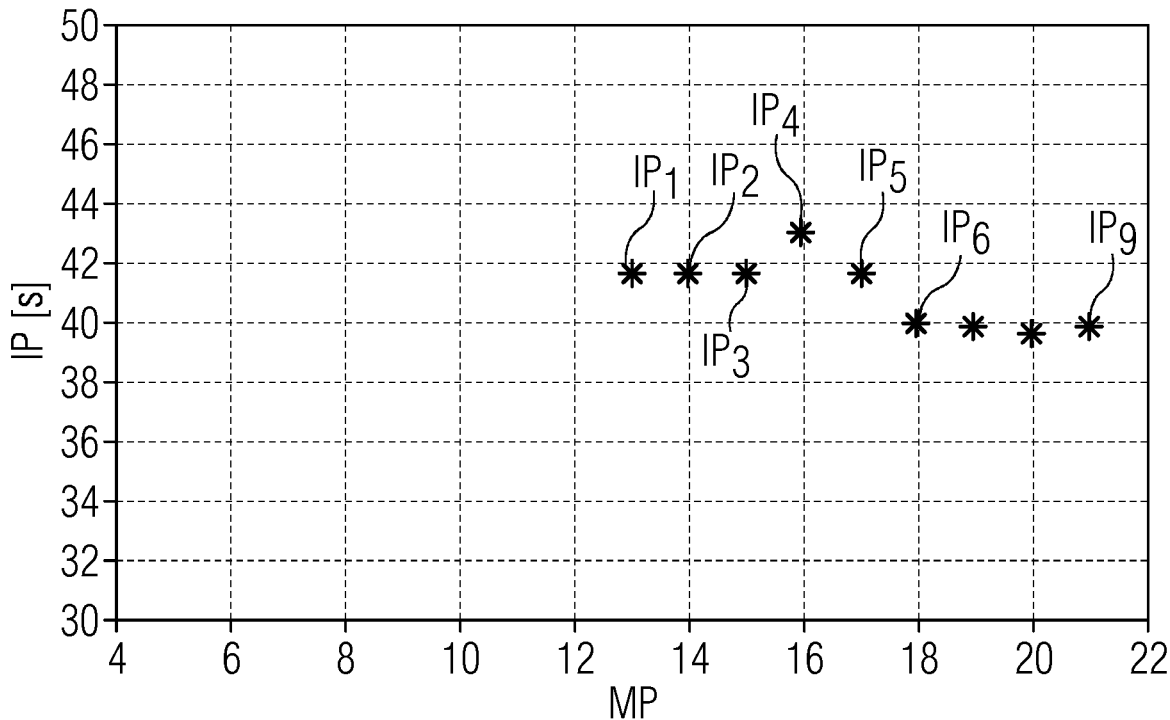
FIG. 11 shows a diagram having a number of contrast medium concentration maxima plotted over the number of concentration value acquisitions.
Figure 12:
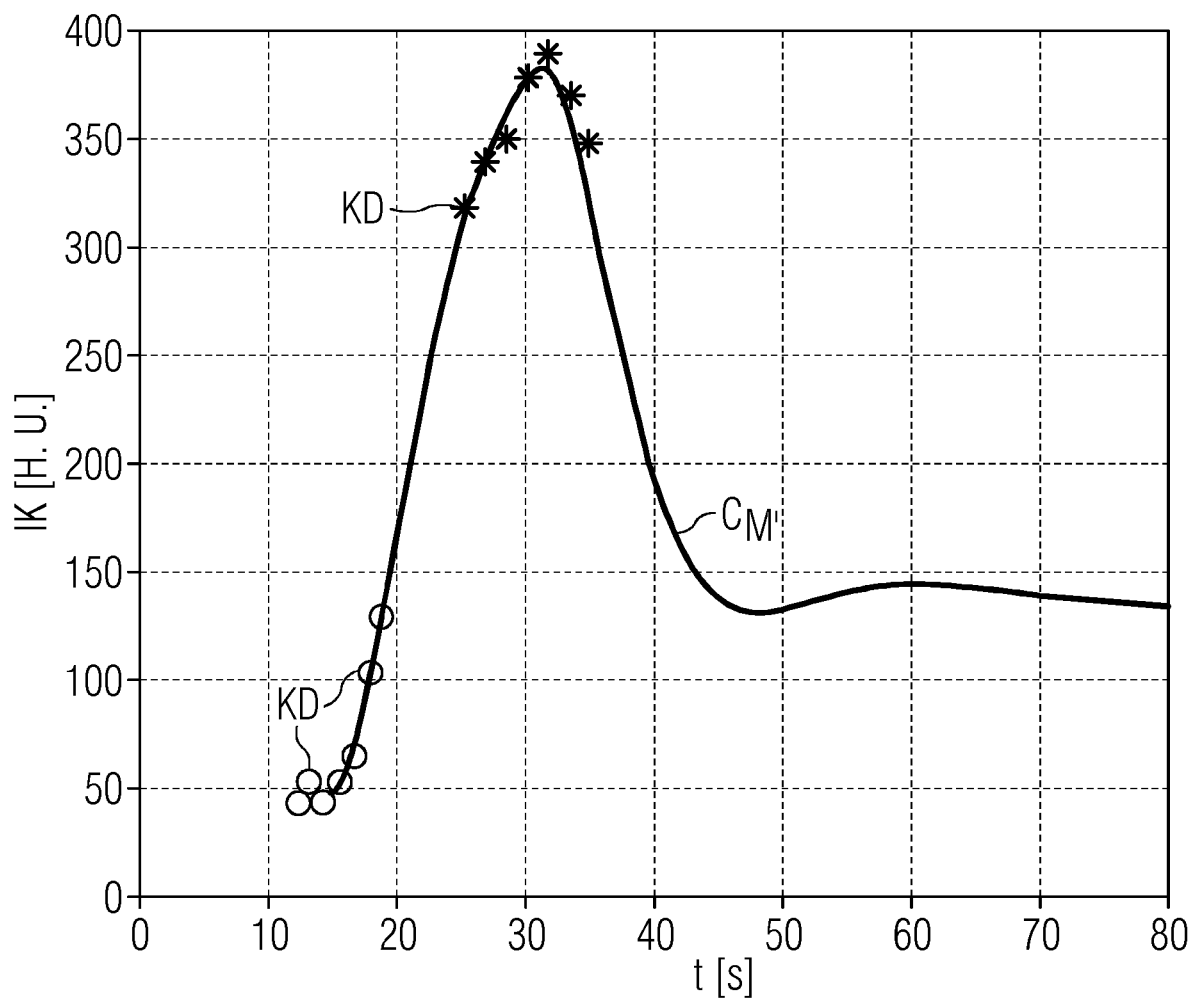
FIG. 12 shows a diagram as in FIG. 4 depicting for comparison purposes concentration values of the bolus tracking scan as well as an examination-specific enhancement model curve determined therefor and actually measured concentration data of the main scan.

In order to ascertain whether the appropriate curve has been found, FIG. 11 shows a change to a contrast medium concentration maximum $IP_1, \ldots, IP_9$ of the examination-specific enhancement model curve $C_M$ calculated by the algorithm (see FIG. 4) in each case following acquisitions of the concentration values $KD_{13}, \ldots, KD_{21}$. According to a first, second and third calculation (at the concentration value measurement points MP 13 to 15), a predicted contrast medium concentration maximum $IP_1$, $IP_2$, $IP_3$ lies at about 42 s after the contrast medium administration start time SK. According to a fourth calculation (at the concentration value measurement point MP 16), the predicted contrast medium concentration maximum $IP_4$ lies at about 43 s after the contrast medium administration start time SK.

The figure shows that after each further acquisition of concentration values $KD_{14}, \ldots, KD_{17}$ after a predefined threshold value is exceeded a calculated contrast medium concentration maximum $IP_2, \ldots, IP_5$ is adjusted until the algorithm after the 18th measurement (of the concentration value $KD_{18}$; at the corresponding 18th concentration value measurement point MP) calculates the concentration peak value $IP_6$ to about 40 s after the contrast medium administration start time SK. This value is confirmed repeatedly in this example by the following measurements and calculations up to and including the 21st measurement (of the concentration value $KD_{21}$; at the corresponding 21st concentration value measurement point MP).

A control device (see FIG. 2) of the CT system 1 used terminates a computing operation performed with the aid of the algorithm and the bolus tracking scan BTS if e.g. the examination-specific enhancement model curve $C_M$ calculated on the basis of a most recently detected concentration value KD exceeds a previously defined reliability threshold value, i.e. therefore predicts with sufficient probability a future profile of an examination-specific enhancement model curve. This can be the case e.g. when two or more successively determined contrast medium concentration maxima IP have substantially constant values (i.e. for example values with a variance below 5%), as is to be observed here in the case of the contrast medium concentration maxima $IP_6$ to $IP_9$. If the reliability threshold value is not reached, the computing operation and the bolus tracking scan BTS are stopped at the latest at a time which guarantees a time buffer which is necessary in order to prepare the scan device before a main measurement HS ("maximum scan delay"). For example, the time buffer enables a patient table of the CT system to be relocated following termination of the bolus tracking scan BTS into a suitable position for performing the main measurement HS.

In order to confirm the reliability of the method, FIG. 12 shows once again an examination-specific enhancement model curve $C_{M'}$ which, in contrast to the examination-specific enhancement model curve $C_M$ according to FIG. 7, was calculated using other actual values. The predicted curve profile was verified via an acquisition of concentration values KD after the event (identified by asterisks; in contrast to the concentration values KD marked by circles, which served for the calculation of the examination-specific enhancement model curve $C_{M'}$). This proves that a calculation of a peak concentration phase KG on the basis of the algorithm according to the invention (see FIG. 4) also yields realistic results in patients under changed conditions, e.g. a different width value of the contrast medium impulse response function, a different injection protocol and a different kV level.

In conclusion it is pointed out once again that the devices described in detail in the foregoing are merely example embodiments which can be modified in a host of different ways by the person skilled in the art without leaving the scope of the invention. Furthermore, the use of the indefinite articles "a" or "an" does not exclude the possibility that the features in question may also be present more than once. Equally, the term "unit" does not rule out the possibility that this consists of a plurality of cooperating subcomponents, which where necessary may also be spatially distributed.

The invention claimed is:

1. A method for determining a measurement start time for an imaging measurement via a medical imaging system, the method comprising:
respectively detecting concentration values of a current concentration of a contrast medium in a monitored region of an examination subject at successive detection times;
determining a current examination-specific enhancement model curve based on a behavior of the concentration values with respect to time and a plurality of candidate enhancement model curves, the plurality of candidate enhancement model curves being calculated based on a population-averaged enhancement model curve; and
determining the measurement start time based on the current examination-specific enhancement model curve,
wherein the determining a current examination-specific enhancement model curve includes,
fitting the concentration values with respect to time to each of the plurality of candidate enhancement model curves, and
selecting the current examination-specific enhancement model curve from among the plurality of candidate enhancement model curves based on the fitting.

2. The method of claim 1, wherein the determining a current examination-specific enhancement model curve is further based on a population-averaged contrast medium impulse response function.

3. The method of claim 2, further comprising:
acquiring injection protocol data, wherein
the determining a current examination-specific enhancement model curve is further based on the injection protocol data.

4. The method of claim 2, wherein a correction factor of each respective one of the plurality of candidate enhancement model curves is chosen such that candidate enhancement model curves having different widths have a substantially identical integral value.

5. The method of claim 2, wherein a correction factor is based on at least one of a current iodine concentration of the contrast medium or a current tube voltage of a computed tomography system used for a current measurement.

6. A method for activating a medical imaging system to generate image data of an examination subject, the method comprising:
determining a measurement start time according to the method of claim 2; and
activating the medical imaging system to generate image data of an examination subject based on the measurement start time.

7. A non-transitory computer readable medium, loadable directly into a memory of a control device of a medical imaging system, the non-transitory computer readable medium including program code segments for performing the method of claim 2 when executed on the control device.

8. The method of claim 1, further comprising:
acquiring injection protocol data, and wherein
the determining a current examination-specific enhancement model curve is further based on the injection protocol data.

9. The method of claim 1, wherein the plurality of candidate enhancement model curves are parameterized by different widths.

10. The method of claim 9, wherein a correction factor of each respective one of the plurality of candidate enhancement model curves is chosen such that candidate enhancement model curves having different widths have a substantially identical integral value.

11. The method of claim 10, wherein the correction factor is based on at least one of a current iodine concentration of the contrast medium or a current tube voltage of a computed tomography system used for a current measurement.

12. The method of claim 1, wherein the population-averaged enhancement model curve includes at least one of a gender-specific population-averaged enhancement model curve, a weight-specific population-averaged enhancement model curve, a size-specific population-averaged enhancement model curve, a defect-specific population-averaged enhancement model curve or an age-specific population-averaged enhancement model curve.

13. The method of claim 1, wherein the plurality of candidate enhancement model curves are parameterized by at least one correction factor.

14. The method of claim 13, wherein the at least one correction factor is based on at least one of a current iodine concentration of the contrast medium or a current tube voltage of a computed tomography system used for a current measurement.

15. The method of claim 13, wherein a respective correction factor among the at least one correction factor is chosen for each of the plurality of candidate enhancement model curves such that candidate enhancement model curves having different widths have a substantially identical integral value.

16. A method for activating a medical imaging system to generate image data of an examination subject, the method comprising:
   determining a measurement start time for an imaging measurement according to the method of claim 1; and
   activating the medical imaging system to generate image data of the examination subject based on the measurement start time.

17. The method of claim 16, wherein the activating the medical imaging system comprises:
   performing an imaging measurement of a target region of the examination subject based on the measurement start time.

18. A non-transitory computer readable medium, loadable directly into a memory of a control device of a medical imaging system, the non-transitory computer readable medium including program code segments for performing the method of claim 16 when executed on the control device.

19. A non-transitory computer readable medium, loadable directly into a memory of a control device of a medical imaging system, the non-transitory computer readable medium including program code segments for performing the method of claim 1 when executed on the control device.

20. The method of claim 1, wherein the selecting selects a closest fitting candidate enhancement model curve from among the plurality of candidate enhancement model curves as the current examination-specific enhancement model curve based on the fitting.

21. The method of claim 1, wherein the concentration values include at least two data values with respect to time, and each of the candidate enhancement model curves includes at least two data values with respect to time.

22. The method of claim 1, wherein each of the plurality of candidate enhancement model curves has a parameter corresponding to cardiac output, and each of the plurality of candidate enhancement model curves has a different value of the parameter.

23. The method of claim 22, wherein the parameter corresponds to a width of a respective candidate enhancement model curve among the plurality of candidate enhancement model curves in a time dimension.

24. A method for performing an imaging measurement via a medical imaging system, the method comprising:
   respectively detecting concentration values of a current concentration of a contrast medium in a monitored region of an examination subject at successive detection times;
   determining a current examination-specific enhancement model curve based on a behavior of the concentration values with respect to time and a plurality of candidate enhancement model curves, the plurality of candidate enhancement model curves being calculated based on a population-averaged enhancement model curve;
   determining a measurement start time for the imaging measurement based on the current examination-specific enhancement model curve; and
   performing the imaging measurement at the measurement start time after the determining the measurement start time, wherein
      the determining a current examination-specific enhancement model curve includes fitting the plurality of candidate enhancement model curves to the behavior of the concentration values with respect to time.

25. The method of claim 24, wherein the fitting comprises at least one of:
   shifting the plurality of candidate enhancement model curves relative to the concentration values with respect to a reference concentration value; or
   shifting the plurality of candidate enhancement model curves relative to the concentration values with respect to a reference time.

26. A control device for a medical imaging system, the control device comprising:
   an interface configured to acquire or output a contrast medium administration start time; and
   a measurement start time determination unit including
      an input interface configured to respectively acquire concentration values of a current concentration of a contrast medium in a monitored region of an examination subject at successive detection times,
      an enhancement model curve determination unit configured to determine a current examination-specific enhancement model curve based on a behavior of the concentration values with respect to time and a plurality of candidate enhancement model curves, the plurality of candidate enhancement model curves being calculated based on a population-averaged enhancement model curve, and
      a model curve analysis unit configured to determine the measurement start time based on the current examination-specific enhancement model curve, wherein
      the enhancement model curve determination unit is configured to determine the current examination-specific enhancement model curve by,
         fitting the concentration values with respect to time to each of the plurality of candidate enhancement model curves, and
         selecting the current examination-specific enhancement model curve from among the plurality of candidate enhancement model curves based on the fitting.

27. A medical imaging system for generating image data of a target region located inside an examination subject, the medical imaging system comprising the control device of claim 26.

* * * * *